United States Patent

Lebreton et al.

[19]

[11] Patent Number: 5,883,132

[45] Date of Patent: Mar. 16, 1999

[54] 15-DEOXYSPERGUALIN ANALOGS, THEIR USE IN THERAPEUTICS AND THEIR METHOD OF PREPARATION

[75] Inventors: Luc Lebreton, Dijon; Patrice Renaut, Hauteville-Lès-Dijon; Philippe Durand, Levallois-Perret, all of France

[73] Assignee: Fournier Industrie Et Sante, Paris, France

[21] Appl. No.: 722,168

[22] PCT Filed: Feb. 7, 1996

[86] PCT No.: PCT/FR96/00203

§ 371 Date: Oct. 10, 1996

§ 102(e) Date: Oct. 10, 1996

[87] PCT Pub. No.: WO96/24579

PCT Pub. Date: Aug. 15, 1996

[30] Foreign Application Priority Data

Feb. 10, 1995 [FR] France ................................ 95/01553
Aug. 17, 1995 [FR] France ................................ 95/09884

[51] Int. Cl.$^6$ ...................... C07C 231/14; C07C 231/18; A61K 31/16
[52] U.S. Cl. .......................... 514/616; 514/825; 514/895; 514/903; 564/138; 564/141; 564/159
[58] Field of Search ...................... 564/159, 138, 564/141; 514/616, 825, 895, 903

[56] References Cited

U.S. PATENT DOCUMENTS

| | | | |
|---|---|---|---|
| 4,525,299 | 6/1985 | Umezawa et al. | 260/112.5 |
| 5,061,787 | 10/1991 | Saino et al. | 564/139 |

FOREIGN PATENT DOCUMENTS

| | | |
|---|---|---|
| 0105193 | 4/1984 | European Pat. Off. . |
| 0181592 | 5/1986 | European Pat. Off. . |
| 2698628 | 6/1994 | France . |

OTHER PUBLICATIONS

The Journal of Antibiotics, vol. XL, No. 9, "Synthesis and Antitumor Activity . . . ", pp. 1303–1315, Sep. 1987.

Annals New York Academy of Sciences, "Synthesis and Background Chemistry . . . ", pp. 123–201, vol. 685.

*Primary Examiner*—Peter O'Sullivan
*Attorney, Agent, or Firm*—Jacobson, Price, Holman & Stern, PLLC

[57] ABSTRACT

The present invention relates to compounds selected from the group consisting of:
(i) the compounds of the formula $$\underset{H_2N}{\overset{NH}{\|}}\underset{N}{\overset{}{\diagdown}}\underset{H}{\overset{(CH_2)_6}{\diagup}}\underset{\overset{}{\underset{C}{\|}}}{\overset{H}{\underset{}{\diagdown}}}\underset{\overset{O}{\|}}{\overset{}{\underset{}{N}}}\underset{CH}{\overset{}{\diagdown}}\underset{\overset{}{\underset{R}{\|}}}{\overset{C}{\underset{}{\diagup}}}\underset{\overset{}{\underset{H}{\|}}}{\overset{(CH_2)_4}{\diagdown}}\underset{N}{\overset{}{\underset{H}{\|}}}\underset{CH}{\overset{(CH_2)_2}{\diagdown}}\underset{CH_3}{\overset{**}{\underset{}{\diagup}}}NH_2 \quad (I)$$

in which:

R is a hydrogen atom, a group OH, a group $OCH_3$ or a group $CH_2OH$,

*C, in the case where R is not a hydrogen atom, is an asymmetric carbon atom of (R,S), (R) or (S) configuration, and

**C is an asymmetric carbon atom of (R,S) or (R) configuration; and (ii) their addition salts.

It further relates to the method of preparing these compounds, to their use in therapeutics and in the field of analysis, and to intermediates.

17 Claims, No Drawings

15-DEOXYSPERGUALIN ANALOGS, THEIR USE IN THERAPEUTICS AND THEIR METHOD OF PREPARATION

FIELD OF THE INVENTION

The present invention relates, by way of novel industrial products, to compounds whose structure is related to that of 15-deoxyspergualin, which has the nomenclature 7-[(aminoiminomethyl)amino]-N-[2-[[4-[(3-aminopropyl)amino]-butyl]amino]-1-hydroxy-2-oxoethyl]heptanamide. It further relates to their method of preparation and to their use in therapeutics.

PRIOR ART

15-Deoxyspergualin (DSG), also known by the international non-proprietary name "Gusperimus", is known to possess a valuable activity in the field of immunosuppression. Numerous publications refer to this activity: in particular, a series of articles on this subject may be found in "Immunomodulating Drugs"—Annals of the New York Academy of Sciences, vol. 685, pages 123 to 201.

However, 15-deoxyspergualin does not have a satisfactory chemical stability and attempts have been made to obtain compounds of greater stability, for example (i) by replacing the α-hydroxyglycine group of 15-deoxyspergualin with various α- or ω-amino acids, (ii) by modifying the structure of the central portion of the chain, or else (iii) by modifying the portion of the chain carrying the guanidine group. Examples of such modifications are described in EP-A-0 181 592, EP-A-0 105 193 and FR-A-2 698 628.

The modifications involving the spermidine portion of the chain were studied essentially in J. Antibiot. 40, pages 1303–1315, and most of the compounds prepared were inactive. None of the proposed structures showed an activity which was at least equivalent to that of DSG, and the authors concluded that the presence of the spermidine linkage was essential.

The present invention relates to compounds which are analogous to 15-deoxyspergualin but in which the spermidine linkage has been modified, said compounds having a greater activity than the known products.

SUBJECT OF THE INVENTION

The present invention proposes novel compounds whose general structure is related to that of 15-deoxyspergualin and which have a greater activity than the known products of the prior art in the field of immunosuppression.

The difference between the products according to the invention and the known products of the prior art derives especially from the presence of a methyl group on the carbon atom carrying the primary amine group of the spermidine portion of the molecule. The choice of a particular configuration for this asymmetric carbon atom (denoted by **C hereafter) also makes it possible to improve the activity of these novel compounds.

The 15-deoxyspergualin analogs according to the invention are characterized in that they are selected from the group consisting of:

(i) the products of the formula

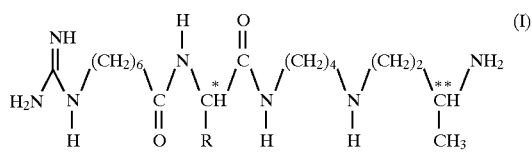

in which:

R is a hydrogen atom, a group OH, a group $OCH_3$ or a group $CH_2OH$,

*C, in the case where R is not a hydrogen atom, is an asymmetric carbon atom of (R, S), (R) or (S) configuration, and

**C is an asymmetric carbon atom of undetermined (R,S) or (R) configuration; and (ii) their addition salts.

According to the invention, a method of preparing the compounds of formula (I) and their addition salts is also recommended, said method comprising the deprotection of a compound of the formula

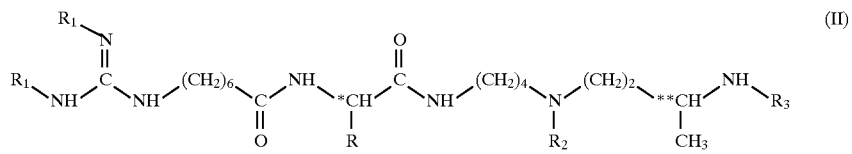

in which:

R is a hydrogen atom, a group $OCH_3$, a group OH, a group $CH_2OH$, a group OR' or a group $CH_2OR'$, R' is a protecting group for the hydroxyl group, $R_1$, $R_2$ and $R_3$, which are identical or different, are each a protecting group for the amine group,

*C, when R is not the hydrogen atom, is an asymmetric carbon atom of (R,S), (R) or (S) configuration, and

**C is an asymmetric carbon atom of (R,S) or (R) configuration, by one or more reaction treatments known to those skilled in the art, in order to effect the replacement of all the protecting groups $R_1$, $R_2$, $R_3$ and R' with a hydrogen atom.

According to the invention, a method of preparing the compounds of formula (I) in which *C is of determined (R) or (S) configuration and R is OH, and their addition salts, is also recommended, said method being applicable to the preparation of 11-(S)-15-DSG (S isomer of 15-deoxyspergualin) and comprising the step which consists in obtaining, as an intermediate, a mixture of diastereoisomers of the formula

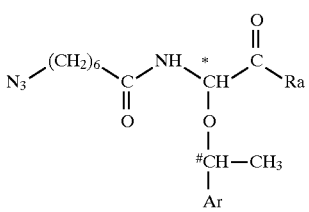

in which:
- Ar is an aromatic substituent, especially a naphthalenyl (i.e. naphthyl) group and preferably the 2-naphthalenyl group,
- Ra is a $C_1$–$C_3$-alkoxy group or a group —HN—$(CH_2)_4$—N($R_2$)—$(CH_2)_2$—CH($CH_3$)—NH($R_3$),
- $R_1$, $R_2$ and $R_3$, which are identical or different, are each an amino-protecting group, especially of the benzyloxycarbonyl type,
- *C is a carbon atom of undetermined (R,S) configuration, and
- #C is a carbon atom of determined (R) or (S) absolute configuration, and separating the two isomers by methods known to those skilled in the art, for example preparative chromatography on silica gel, to give separately the compounds of the formulae

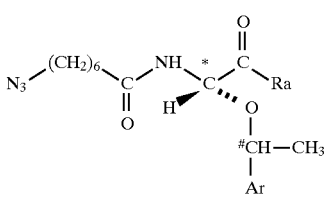

and

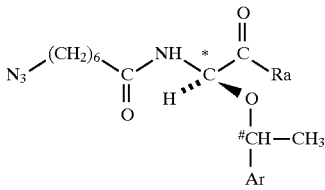

in which Ar, Ra and #C are as defined above.

The compounds of the above formula in which #C is of determined (S) or (R) configuration and Ar, Ra and #C are defined as indicated above are novel and form one of the subjects of the invention.

The use of a substance selected from the compounds of formula I and their non-toxic addition salts is also recommended for obtaining drugs intended for use in therapeutics for the treatment or prevention of immune disorders, hyperreactive inflammatory diseases or malaria, or for use as a pharmacological reagent in the field of analysis.

DETAILED DESCRIPTION OF THE INVENTION

"Addition salts" are understood here as meaning the acid addition salts obtained by reacting a compound of formula I with a mineral acid or an organic acid. The preferred mineral acids for salification are hydrochloric, hydrobromic, phosphoric and sulfuric acids. The preferred organic acids for salification are fumaric, maleic, methanesulfonic, oxalic, citric, acetic and trifluoroacetic acids.

As indicated in formula I, the compounds according to the invention contain a carbon denoted by *C, which is an asymmetric carbon when R is not a hydrogen atom, and a second carbon atom denoted by C, which is also an asymmetric carbon. When R is a hydrogen atom, the compounds of formula I covered by the present invention include the racemate, where C is of (R,S) configuration, and the enantiomer where **C is of (R) configuration. When R is not a hydrogen atom, the compounds of formula I covered by the present invention, which then have two centers of chirality, include (1) the product of [(R,S)—*C; (RS)—**C] configuration, which is a substantially equimolecular mixture of the four stereoisomers, (2) the "hemiracemic" products of [(R,S)—*C; (R)—**C], [(R)—*C; (R,S)—**C] and [(S)—*C; (R,S)—**C] configuration, and (3) the diastereoisomers of [(R)—*C; (R)—**C] and [(S)—*C; (R)—**C] configuration.

In practice, the preferred compounds of formula I according to the invention are those in which **C is of (R) configuration.

The compounds of formula I can be obtained by methods known per se in which conventional reaction mechanisms are applied, especially reactions which are commonly used in peptide chemistry and make it possible to obtain bonds of the amide type.

As indicated above, the method of preparing the compounds of formula I which is recommended according to the invention comprises the deprotection of a compound of formula II.

In practice, the protecting groups $R_1$, $R_2$ and $R_3$ which are to be replaced with a hydrogen atom are amino-protecting groups of a type known in the field of peptide chemistry for temporarily blocking "amine" groups which are not totally substituted. The following may be mentioned in particular among the groups suitable for this purpose:

a) groups of the oxycarbonyl type, for example alkoxycarbonyl and benzyloxycarbonyl groups:
   - Boc: t-butoxycarbonyl (or 1,1-dimethylethoxycarbonyl)
   - Fmoc: 9-fluorenylmethoxycarbonyl
   - Z: benzyloxycarbonyl (or phenylmethoxycarbonyl)
   - Z(p-Cl): 4-chlorobenzyloxycarbonyl, or
   - Z(p-OMe): 4-methoxybenzyloxycarbonyl, on the one hand, and b) groups of the benzyl type, for example the phenylmethyl group (Bn), on the other.

The groups Boc, Z, Fmoc and Bn are preferred among these amino-protecting groups.

When the substituent R in formula I comprises a hydroxyl group, it may be necessary to protect it in order to perform the reactions which yield the compounds of formula II. In this case, R in formula II can have the intermediate meaning of a group OR' or $CH_2OR'$, in which R' is a protecting group for the hydroxyl group. The following may be mentioned in particular among the protecting groups for the hydroxyl group:

a) groups of the benzyl type, for example the phenylmethyl group (Bn), b) groups of the trialkylsilyl type, for example the trimethylsilyl group and the tert-butyldimethylsilyl group (tBDMS) of the formula

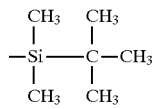

c) the 2-tetrahydropyranyl group, and d) groups of the α-alkylated benzyl type, for example the 1-(naphthalen-2-yl)ethyl group, these groups having the advantage of introducing an asymmetric carbon which is useful for separating the configurational isomers, where necessary.

In practice, the method of preparing a compound of formula I or one of its addition salts is characterized in that it comprises the steps which consist in:
(i) deprotecting a compound of formula II:

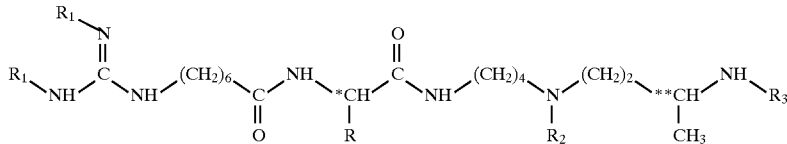

in which:
R is a hydrogen atom, a group O—$CH_3$, a group OH, a group $CH_2OH$, a group OR' or a group $CH_2OR'$,
R' is a trialkylsilyl group, a group of the phenylmethyl type or an α-alkylated benzyl group,
$R_1$, $R_2$ and $R_3$, which are identical or different, are each an amino-protecting group of the alkoxycarbonyl, benzyloxycarbonyl or benzyl type,
*C, when R is not the hydrogen atom, is an asymmetric carbon atom of (R,S), (R) or (S) configuration, and
**C is an asymmetric carbon atom of (R,S) or (R) configuration, by one or more treatments adapted to the nature of the protecting groups, such as, for example, if at least one of the groups $R_1$, $R_2$, $R_3$ and R' is a group of the alkoxycarbonyl or trialkylsilyl type, by reaction with a strong acid such as trifluoroacetic acid in particular, or if at least one of the groups $R_1$, $R_2$, $R_3$ and R' is a group of the benzyl type, by catalytic hydrogenation in the presence of a palladium salt, palladium on charcoal or palladium hydroxide on charcoal, to give a compound of formula I in the form of the free base or one of its addition salts, and, if necessary,
(ii) using an addition salt obtained according to step (i) to obtain the compound of formula I in the form of the free base by reaction with a strong base, and then using said free base to obtain the other addition salts.

Room temperature is understood as meaning a temperature between 15° and 25° C. A temperature close to or around room temperature is understood as meaning a temperature between about 5° and 40° C.

A compound of formula II can be prepared by using a method selected from the following variants:
(a) variant A comprising the steps which consist in:
(i) condensing an acid of the formula

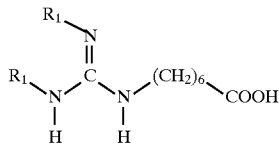
(III)

in which $R_1$ is an amino-protecting group, for example a group Boc, with an amino acid derivative of the formula

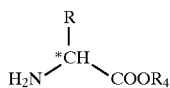
(IV)

in which:
R is a hydrogen atom or a group $CH_2OR'$,
R' is a protecting group for the hydroxyl group, for example a group tBDMS, $R_4$ is a $C_1$–$C_3$-alkyl group, and
*C, when R is not the hydrogen atom, is an asymmetric carbon atom of (R,S) (racemic), (R) or (S) configuration,
by activating the acid group with a coupling agent of the carbodiimide type, especially 1,3-dicyclohexylcarbodiimide (DCC), in the presence of a nucleophilic agent, especially 1-hydroxybenzotriazole (HOBT), in an organic solvent, for example dichloromethane, at a temperature between 0° and 40° C., at a rate of 1 mol of compound III to about 1 mol of compound IV, to give a compound of the formula

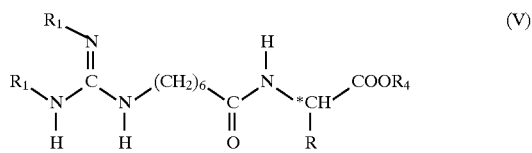
(V)

in which R, $R_1$, $R_4$ and *C are as defined above;
(ii) hydrolyzing the ester group of a resulting compound of formula V,
either according to step (i) above when R is the hydrogen atom or a group $CH_2OR'$ as described above,
or by a known method when R is a group OR', where R' is a protecting group for the hydroxyl group, for example the group tBDMS,
by reaction with a dilute solution of a base, for example sodium hydroxide, in the presence of a water-miscible solvent, for example 1,2-dimethoxyethane, at a temperature around room temperature, for about 2 to 30 minutes, to give a compound of the formula

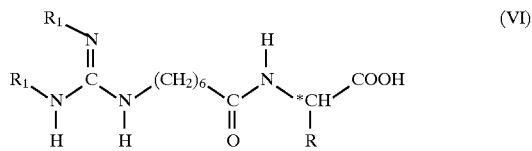
(VI)

in which $R_1$ and *C are as defined in the compound of formula V and R is a hydrogen atom, a group $CH_2OR'$ or a group OR', R' being a protecting group for the hydroxyl group; and
(iii) reacting a compound of formula VI, obtained according to step (ii) above, with a compound of the formula

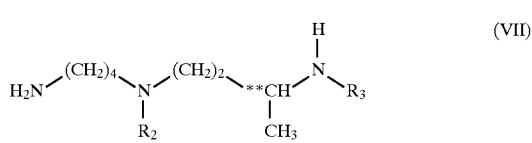
(VII)

in which:
$R_2$ and $R_3$, which are identical or different, are each an amino-protecting group, for example a group Boc or a group Bn, and
**C is an asymmetric carbon of (RS) or (R) configuration, under conditions identical to those described in step (i) above, to give a compound of formula II:

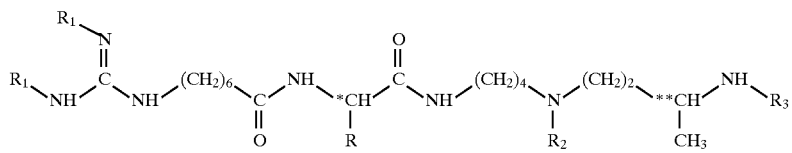

in which R, $R_1$, $R_2$, $R_3$, *C and **C are as defined above;

(b) variant B comprising the steps which consist in:
(i) condensing an amino acid derivative of the formula

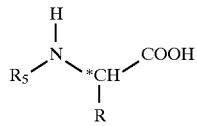

(VIII)

in which:

R is a hydrogen atom or a group $CH_2OR'$, where R' is a protecting group for the hydroxyl group, $R_5$ is an amino-protecting group, for example a group Fmoc, and

*C, when R is not the hydrogen atom, is an asymmetric carbon atom of (R,S), (R) or (S) configuration, with a compound of the formula

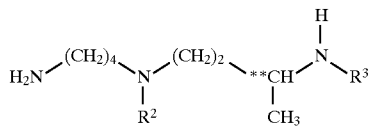

(VII)

in which:

$R_2$ and $R_3$, which are identical or different, are each an amino-protecting group, both being different from the protecting group $R_5$ present in the compound of formula VIII, and

**C is an asymmetric carbon of (R,S) or (R) configuration, under conditions analogous to those of the method of step (i) of variant A above, to give a compound of the formula

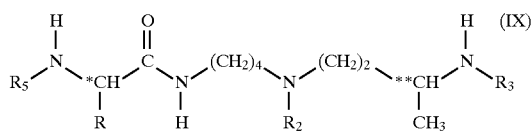

(IX)

in which R, $R_2$, $R_3$, $R_5$, *C and **C are as defined above;
(ii) deprotecting the resulting compound IX by a specific method for scission of the N—$R_5$ bond, for example, if $R_5$ is a group Fmoc, by treatment with piperidine in a solvent, for example dichloromethane, at room temperature, for about 1 to 5 hours, to give a compound of the formula

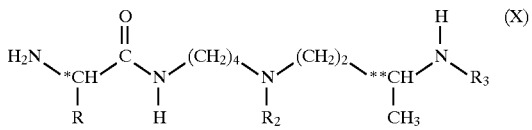

(X)

in which R, $R_2$, $R_3$, *C and **C are as defined above; and
(iii) condensing the resulting amine compound of formula X with an acid of the formula

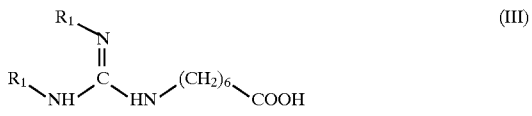

(III)

in which $R_1$ is an amino-protecting group, for example a group Boc, under operating conditions analogous to those described in step (i) of variant A, to give a compound of formula II:

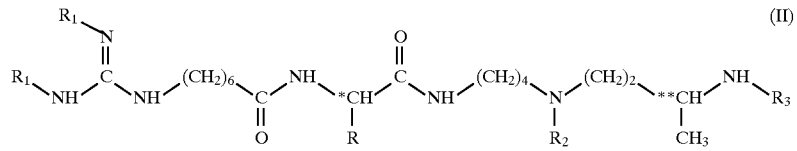

(II)

in which R, $R_1$, $R_2$, $R_3$, *C and **C are as defined above;

(c) variant C comprising the steps which consist in:
($i_a$) reacting 7-azidoheptanamide with methyl 2-hydroxy-2-methoxyacetate of the formula

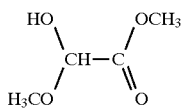

in a solvent of the halogenated hydrocarbon type, especially dichloromethane, in the presence of a dehydrating agent, especially a molecular sieve, at a temperature between 25° C. and the reflux temperature of the solvent, for 10 to 50 hours, to give an intermediate of the formula

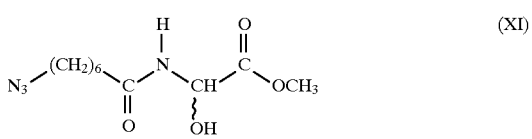

(XI)

($i_b$) reacting the resulting compound of formula M in situ with thionyl chloride, at a temperature of about 40° C., for 1 to 3 hours, to give the halogenated compound of the formula

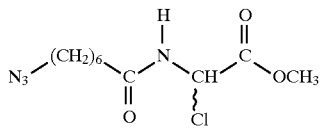
(XII)

($i_c$) reacting the resulting compound of formula XII with a chiral alcohol of determined (R) or (S) configuration, of the benzyl type, for example of the formula

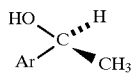
(XIII)

in which Ar is an aromatic radical, especially a naphthalenyl (i.e. naphthyl) group and preferably the 2-naphthalenyl group, in a solvent of the halogenated hydrocarbon type, especially dichloromethane, in the presence of a base, especially triethylamine, at a temperature between 10° and 40° C., for 5 to 50 hours, to give the compound of the formula

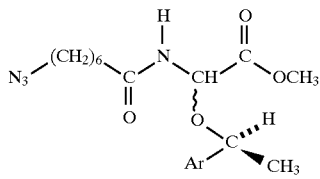
(XIV)

where Ar is as defined in the compound of formula XIII;

(ii) hydrolyzing the ester group of the resulting compound of formula XIV by reaction with a base in an aqueous medium, especially aqueous sodium hydroxide solution, in a solvent of the ether type, especially 1,2-dimethoxyethane, at a temperature around room temperature, to give, after acidification, the acid compound of the formula

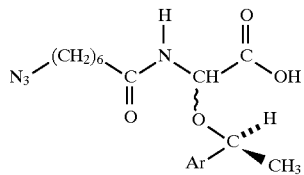
(XV)

in which Ar is as defined above;

(iii) reacting the resulting compound of formula XV with an amine of the formula

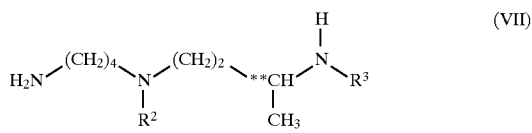
(VII)

in which $R_2$ and $R_3$ are each an amino-protecting group sensitive to hydrogenation, especially a benzyloxycarbonyl group (Z), and **C is an asymmetric carbon of (R,S) or (R) configuration, in a solvent, especially a halogenated hydrocarbon and particularly dichloromethane, in the presence of at least one coupling activator of a type known in peptide synthesis, particularly 1,3-dicyclohexylcarbodiimide (DCC) and 1-hydroxybenzotriazole (HOBT), at a temperature close to room temperature, for 10 to 75 hours, to give a mixture of the 2 diastereoisomers of the formula

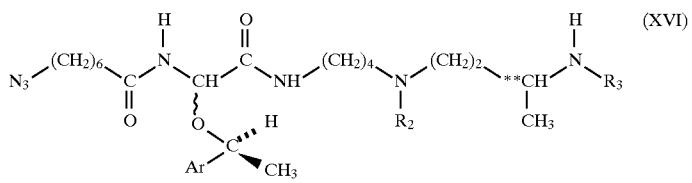
(XVI)

in which Ar, $R_2$, $R_3$ and **C are as defined above; (iv) separating the isomers of the resulting compound of formula XVI, for example by means of chromatography on silica gel, to give each of the following two compounds separately:

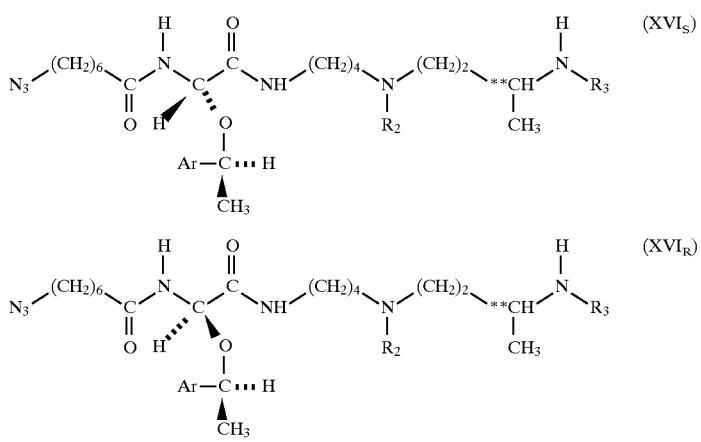

where Ar, $R_1$, $R_2$, $R_3$ and **C are as defined above; and
(v) reacting the resulting compound of formula XVIs with triphenylphosphine, in the presence of water, in an anhydrous solvent, especially tetrahydrofuran, at a temperature between 50° and 70° C., for 10 to 30 hours, to give the corresponding intermediate amine, which is reacted in situ with the compound of the formula

(XVII)

in which $R_1$ is an arnino-protecting group, especially of the benzyloxycarbonyl type, to give, after reaction for 10 to 48 hours at a temperature close to room temperature, the compound of formula II:

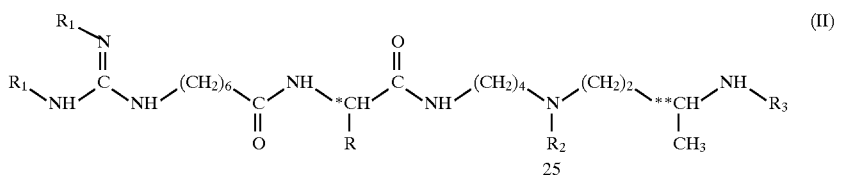

(II)

in which:

R is the group OR', $R_1$, $R_2$ and $R_3$ are each an amino-protecting group, especially of the benzyloxycarbonyl type, R' is a group of the α-methylated benzyl type of the formula

**C is an asymmetric carbon of (R,S) or (R) configuration, and

*C is an asymmetric carbon of (S) configuration; or (d) variant D comprising the steps which consist in:
(i) taking a compound of formula XIV, obtained above according to step ($i_c$) of variant C, and separating its two diastereoisomers, especially by means of chromatography on silica gel, to give separately the two pure isomers of the formulae

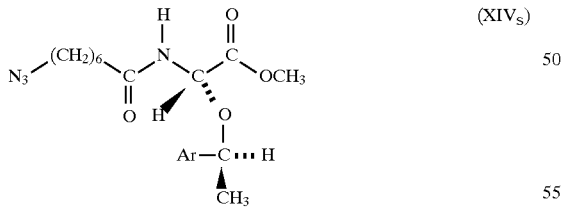

(XIVs)

and

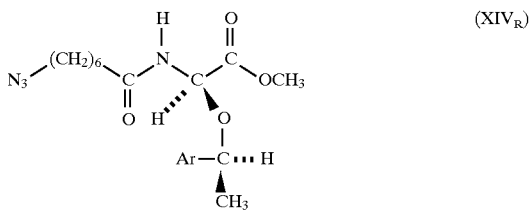

(XIVR)

in which Ar is an aromatic radical as indicated above, especially a naphthalenyl group and preferably the 2-naphthalenyl group;

(ii) hydrolyzing the ester group of the resulting compound XIVs, under conditions identical to those described in step (ii) of variant C, to give the corresponding acid of the formula

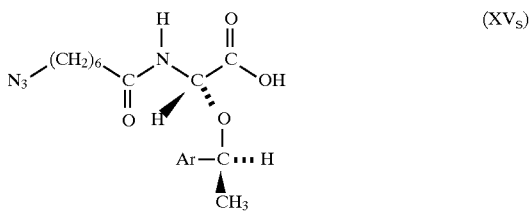

(XVs)

in which Ar is as defined above;

(iii) reacting the resulting compound XVs with an amine of formula VII:

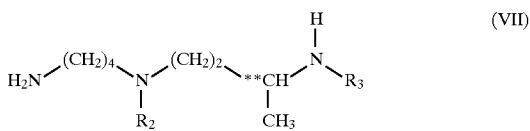

(VII)

in which $R_2$ and $R_3$ are an amino-protecting group sensitive to hydrogenation, for example a benzyloxycarbonyl group (Z), and **C is a carbon of (R,S) or (R) configuration, under conditions identical to those described in step (iii) of variant C, to give the compound of the formula

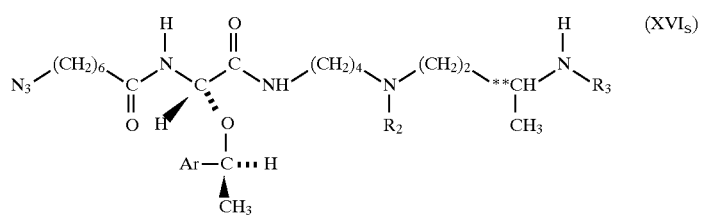

(XVIs)

where Ar, $R_2$, $R_3$ and **C are as defined above; and then
(iv) treating the resulting compound of formula $XVI_S$ in a manner analogous to step (v) of the method according to variant C to give the compound of formula II with the same characteristics as in the case of said variant C.

The above method has been described using a chiral alcohol of formula XIII of (S) configuration, although this method can of course be applied analogously with a chiral alcohol of (R) configuration.

As far as the structure of this alcohol is concerned, "alcohol of the benzyl type" is understood as meaning an alcohol whose hydroxyl group is carried by the first carbon of a substituent of the aromatic ring; thus, for example, a compound like 1-indanol [used in this case in either its (R) or (S) form] is considered to be an alcohol of the benzyl type.

Variants C and D of the method both make it possible to obtain the compounds of formula I in which the carbon *C carrying the hydroxyl group is of determined (R) or (S) configuration and the carbon **C carrying the primary amine group is of (RS) or (R) configuration.

These two variants are also useful in the preparation of all the derivatives of the acids of formula $XV_S$ or $XV_R$ and more particularly the isomers of 15-deoxyspergualin of determined (S) and (R) configuration [i.e. 11-(S)-15-DSG and 11-R)-15-DSG] of the formulae

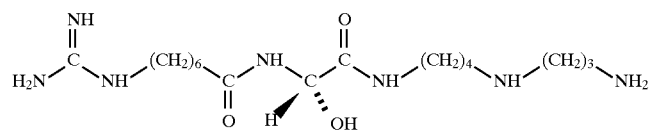

[11-(S)-15-DSG]

and

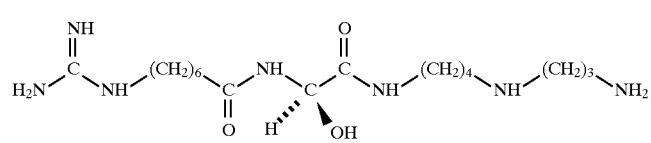

[11-(R)-15-DSG]

and their addition salts.

In fact, using one or other of variants C and D described above, and replacing the amine of formula VII with an analogous spermidine derivative of the formula $NH_2$—$(CH_2)_4$—$N(R_2)$—$(CH_2)_3$—$NH(R_3)$, gives the intermediates of the structure

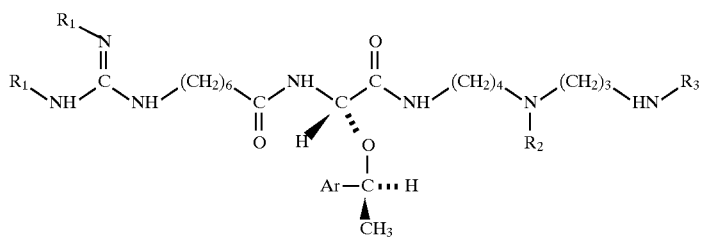

intermediate of (S) configuration, and

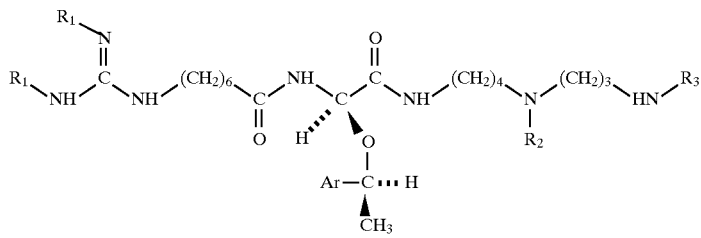

intermediate of (R) configuration, whose structure is related to that of the compounds of formula II (where $R_1$, $R_2$ and $R_3$ are each an amino-protecting group, especially of the benzyloxycarbonyl type, and Ar is defined as indicated above), and then the compounds 11-(R)-15-DSG and 11-(S)-15-DSG with an excellent optical purity.

By way of information and for practical reasons, the principal reaction mechanisms of the synthesis of the isomer 11-(S)-15-DSG according to variant C and variant D are illustrated below in Scheme 1 and Scheme 2 respectively.

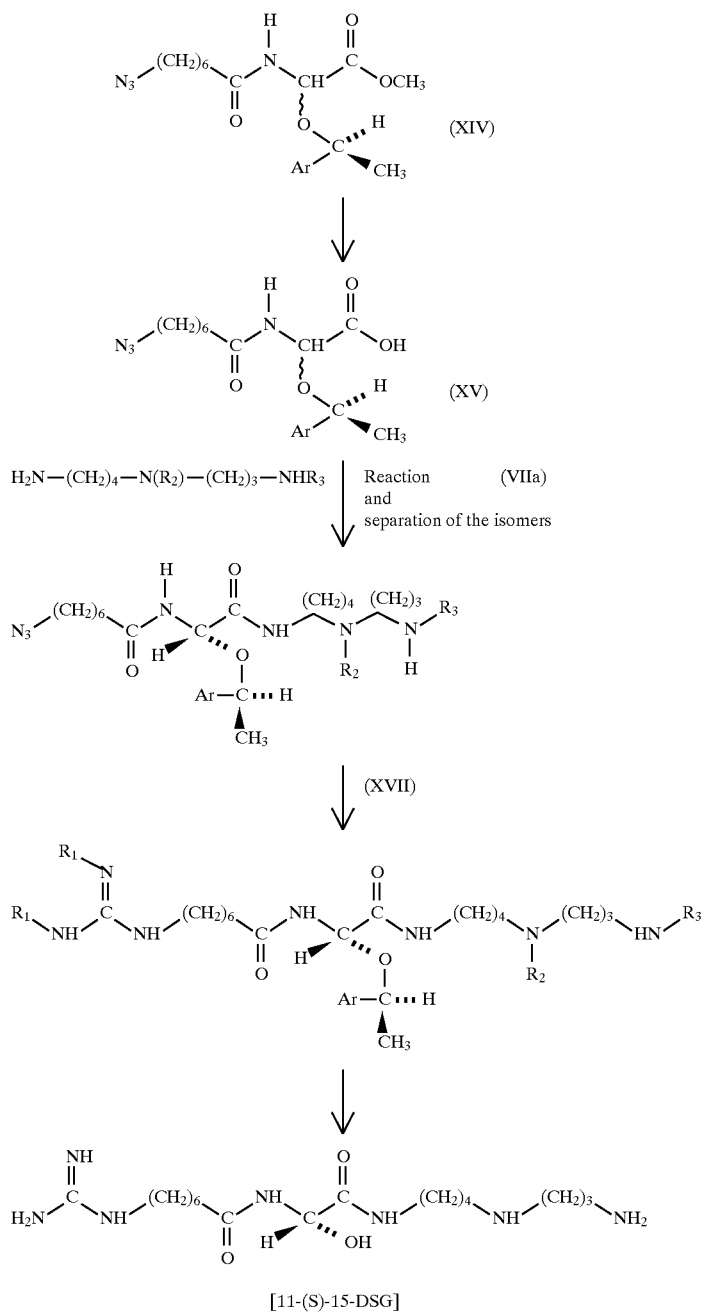

Scheme 2: variant D
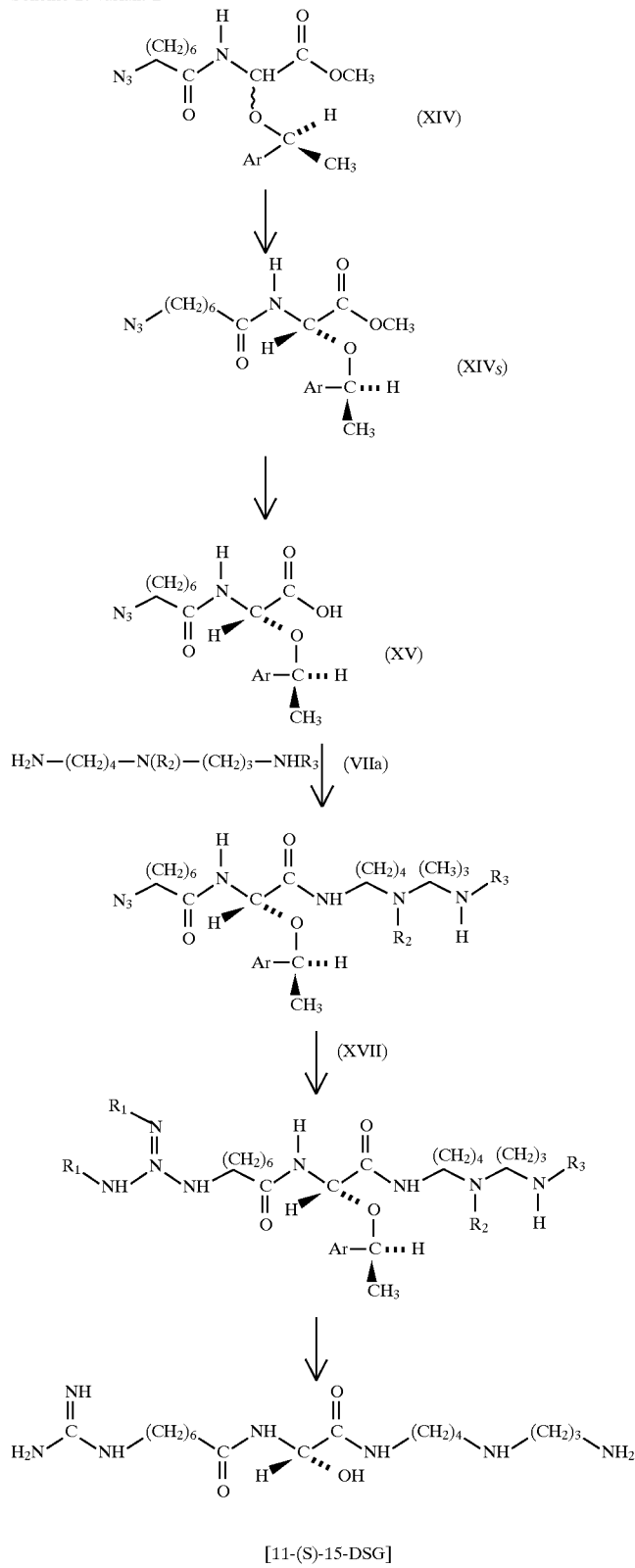
[11-(S)-15-DSG]
The acid of formula III in which $R_1$ is the 1,1-dimethylethoxycarbonyl group (Boc) is prepared by reacting 7-arninoheptanol with N,N'-bis(Boc)-S-methylisothiourea and then oxidizing the resulting alcohol with pyridinium dichromate in dimethylformamide.

The compounds of formula VII in which $R_2$ and $R_3$ are identical and are each the group Boc can be obtained from a compound of the formula

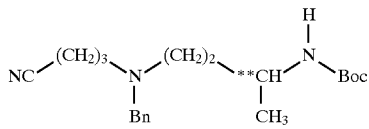

in which:
Bn is the phenylmethyl group,
Boc is the 1,1-dimethylethoxycarbonyl group, and
**C is an asymmetric carbon atom of (RS) or (R) configuration, by catalytic hydrogenation in the presence of palladium on charcoal, enabling the group Bn to be replaced with a hydrogen atom, then reaction with di(tert-butyl) dicarbonate to give the compound of the formula

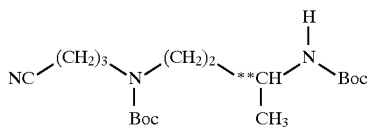

and, finally, catalytic hydrogenation of the cyano group, in the presence of Raney nickel, to give the expected compound of formula VII.

The compounds of formula VII in which $R_2$ and $R_3$ are identical and are each a phenylmethoxycarbonyl amino-protecting group (commonly called Z) can be obtained from a compound of the formula

by protection of the free amine with an amino-protecting group sensitive to alkaline media (and stable in acid media), for example a trifluoroacetyl group, followed by freeing of the other two amine groups by reaction with an acid and then with hydrogen, respectively, protection of these free amine groups with the phenylmethoxycarbonyl group and, finally, reaction with a base to effect the replacement of the amino-protecting group sensitive to alkaline media with a hydrogen atom.

The compounds of formula VII in which $R_2$ and $R_3$ are a group Boc or a group Z are novel and form one of the subjects of the invention. They serve as synthesis intermediates for obtaining the compounds of formula I according to the invention.

The invention will be understood more clearly from the following Examples and the results of pharmacological tests obtained with the compounds according to the invention, compared with the results obtained with known products of the prior art. The nomenclature used in the Examples is the one recommended by Chemical Abstracts; thus an ester of the type "t-butyl . . . -oate" will be written in the form " . . . -oic acid, 1,1-dimethylethyl ester".

In the experimental section, the Preparations relate to the intermediates and the Examples relate to the products according to the invention.

If the compounds contain an asymmetric carbon in their structure, the absence of any particular notation or the notation (R,S) indicates that they are a substantially equimolecular mixture of the two enantiomers (i.e. "racemic" compound). If these same compounds are named with the symbol (R) or (S) immediately following the identification of the position of a substituent, this means that the carbon carrying this substituent is of (R) or (S) configuration in accordance with the Cahn, Ingold and Prelog rules.

If the compounds contain two centers of asymmetry in their structure, the absence of any particular notation or the presence of the symbol (R,S) immediately following the identification of the positions of the substituents means that they are a mixture of the four stereoisomers. If these same compounds are named with the symbol (R) or (S) immediately following the identification of the position of a substituent, this means that the carbon carrying this substituent is of determined (R) or (S) configuration; if only one of the centers of asymmetry is named with a chirality symbol, the product described will be a substantially equimolecular mixture of the two diastereoisomers. If both the centers of asymmetry are named with a chirality symbol, the product described is a pure stereoisomer.

The spectral characteristics of the nuclear magnetic resonance (NMR) signals are given for the proton ($^1$H) or for the 13 isotope of carbon ($^{13}$C) and are indicated as follows: the chemical shift relative to the tetramethylsilane signal and, in brackets, the shape of the signal (s for singlet, d for doublet, t for triplet, q for quadruplet, m for multiplet, bs for broad signal) and the number of protons to which the signal relates. By way of indication, the $^1$H NMR spectra were run at 300 MHz.

PREPARATION I

[(7-Hydroxyheptyl)carbonimidoyl]bis(carbamic) acid, bis(1,1-dimethylethyl) Ester 4.57 g ($35.10^{-3}$ mol) of 7-aminoheptanol and 10.15 g ($35.10^{-3}$ mol) of [[[(1,1-dimethylethoxy)carbonyl]amino] (methylthio)methylene]carbamic acid, 1,1-dimethylethyl ester are dissolved in 400 ml of tetrahydrofuran and the solution is stirred for 15 hours at room temperature. The reaction mixture is concentrated under reduced pressure and purified by chromatography on silica gel using a methylcyclohexane/ethyl acetate mixture (7/3 v/v) as the eluent to give 12.6 g of the expected product in the form of a yellow oil (yield=96%).
$^1$H NMR (CDCl$_3$): 1.25–1.6 (m, 28H); 3.35–3.45 (q, 2H); 3.63 (q, 2H); 8.25 (t, 1H); 11.5 (s, 1H).

PREPARATION II

[(6-Carboxyhexyl)carbonimidoyl]bis(carbamic) acid, bis(1,1-dimethylethyl) ester 12.6 g ($33.7.10^{-3}$ mol) of the compound obtained according to Preparation I are dissolved in 100 ml of dimethylformamide, and 25.2 g ($67.10^{-3}$ mol) of pyridinium dichromate are added. The reaction medium is stirred for 2 hours at room temperature and then hydrolyzed with 1 l of water. It is extracted 3 times with diethyl ether and the combined organic phases are washed with copper sulfate solution and then with water. The resulting organic phase is subsequently dried over magnesium sulfate and then concentrated under reduced pressure to give 12 g of the expected product in the form of an oil (yield=91.6%).
$^1$H NMR (CDCl$_3$): 1.25–1.70 (m, 26H); 2.35 (t, 2H); 3.40 (q, 2H); 8.30 (t, 1H); 11.5 (bs, 1H).

PREPARATION III

3-[[(1,1-Dimethylethoxy)carbonyl]amino]-11-oxo-2, 4,12-triazatetradec-2-enedioic Acid, 1-(1,1-dimethylethyl) 14-ethyl ester A solution of 5.28 g ($13.64.10^{-3}$ mol) of the compound obtained according to Preparation II in 80 ml of dichloromethane is prepared. The solution is cooled to 0° C. and 1.84 g (13.64.10$^{-3}$ mol) of 1-hydroxybenzotriazole (HOBT) hydrate and 5.63 g (27.28.10$^{-3}$ mol) of N,N'-dicyclohexylcarbodiimide (DCC) are then added, followed by a solution of 2.1 g (15.10$^{-3}$ mol) of ethyl glycinate hydrochloride and 1.51 g (15.10$^{-3}$ mol) of triethylamine in 20 ml of dichloromethane. The reaction mixture is stirred for 48 hours at room temperature and then concentrated under reduced pressure. The residue is then purified by chromatography on silica gel using a methylcyclohexane/ethyl acetate mixture (6/4 v/v) as the eluent to give 4.41 g of the expected product in the form of a colorless oil (yield=68.6%).

$^1$H NMR (CDCl$_3$): 1.25 (t, 3H); 1.3–1.8 (m, 26H); 2.25 (t, 2H); 3.4 (t, 2H); 4.0 (d, 2H); 4.2 (q, 2H); 6.0 (bs, 1H); 8.3 (t, 1H); 11.5 (s, 1H).

PREPARATION IV

3-[[(1,1-Dimethylethoxy)carbonyl]amino]-11-oxo-2,4,12-triazatetradec-2-enedioic Acid, 1-(1,1-dimethylethyl) ester 4.41 g (9.34.10$^{-3}$ mol) of the compound obtained according to Preparation III are dissolved in 15 ml of 1,2-dimethoxyethane, and 15 ml of 1N sodium hydroxide are then added. The mixture is stirred at room temperature (advantageously at 20°–25° C.) for 30 minutes, 100 ml of dichloromethane are then added and the mixture is acidified carefully to pH 1 with 1N hydrochloric acid, with cooling and thorough stirring. The organic phase is decanted and the aqueous phase is then extracted twice with 100 ml of dichloromethane. The combined organic phases are dried over magnesium sulfate and then concentrated under reduced pressure to give 4.1 g of the expected product in the form of a yellow oil (yield=99%).

$^1$H NMR (CDCl$_3$): 1.3–1.8 (m, 26H); 2.25 (t, 2H); 3.3–3.35 (m, 2H); 4.0 (d, 2H); 6.5 (t, 1H); 8.45 (bs, 1H); 11.5 (s, 1H).

PREPARATION V

3-[[(1,1-Dimethylethoxy)carbonyl]amino]-23-(R)-methyl-20-phenylmethyl-11,14-dioxo-2,4,12,15,20,24-hexaazapentacos-2-enedioic Acid, bis(1,1-dimethylethyl) ester 4.1 g (9.23.10$^{-3}$ mol) of the product obtained according to Preparation IV are dissolved in 100 ml of dichloromethane, 1.35 g (10.10$^{-3}$ mol) of HOBT and 4.13 g (20.10$^{-3}$ mol) of DCC are then added and the mixture is stirred at 0° C. for 30 minutes. 3.3 g (9.45.10$^{-3}$ mol) of [3-[(4-aminobutyl)(phenylmethyl)amino]-1-(R)-methylpropyl] carbamic acid, 1,1-dimethylethyl ester are then added and the reaction medium is then stirred for 24 hours at room temperature. After concentration under reduced pressure, the residue is purified by chromatography on silica gel using an ethyl acetate/ethanol mixture (9/1 v/v) as the eluent to give 5.9 g of the expected product in the form of an amorphous white solid (yield=82.5%). [α]$_D^{24.5}$=+0.44° (c=0.45; CHCl$_3$).

$^1$H NMR (DMSO-d$_6$): 0.95 (d, 3H); 1.2–1.7 (m, 41H); 2.1 (t, 2H); 2.3–2.45 (m, 4H); 3.0–3.1 (m, 2H); 3.2–3.4 (m, 4H); 3.4–3.5 (m, 1H); 3.6 (d, 2H); 6.65 (d, 1H); 7.25–7.35 (m, 5H); 7.7 (t, 1H); 7.95 (t, 1H); 8.3 (t, 1H); 11.5 (s, 1H).

PREPARATION VI

3-[[(1,1-Dimethylethoxy)carbonyl]amino]-23-(R)-methyl-11,14-dioxo-2,4,12,15,20,24-hexaazapentacos-2-enedioic Acid, bis(1,1-dimethylethyl) ester 5.9 g (7.61.10$^{-3}$ mol) of the compound obtained according to Preparation V are dissolved in 120 ml of pure ethanol, 500 mg of 5% palladium on charcoal are added and the mixture is stirred under a hydrogen atmosphere for 8 hours at room temperature. The catalyst is subsequently filtered off and the filtrate is then concentrated under reduced pressure to give 4.94 g of the expected product in the form of an amorphous solid (yield=95%).

[α]$_D^{24}$=−4.8° (c=1.00; CHCl$_3$).

$^1$H NMR (DMSO-d$_6$): 1.05 (d, 3H); 1.2–1.8 (m, 41H); 2.17 (t, 2H); 2.7–2.85 (m, 4H); 3.0–3.15 (m, 2H); 3.25–3.4 (m, 3H); 3.45–3.55 (m, 1H); 3.6 (d, 2H); 6.35 (d, 1H); 7.85 (t, 1H); 8.0 (t, 1H); 8.3 (t, 1H); 11.5 (bs, 1H).

EXAMPLE 1

N-[2-[[4-[(3-(R)-Aminobutyl)amino]butyl]amino]-2-oxoethyl]-7-[(aminoiminomethyl)amino] heptanamide tris(trifluoroacetate)

A mixture of 4 g (5.83.10$^{-3}$ mol) of the compound obtained according to Preparation VI, 25 ml of dichloromethane and 25 ml of trifluoroacetic acid is prepared and stirred at room temperature for 5 hours. The reaction mixture is then concentrated under reduced pressure and the evaporation residue is purified by medium pressure chromatography (MPLC) using a grafted silica gel [of the RP18 type (particle size: 5 to 20 μm)]. The eluent is an acetonitrile/water/trifluoroacetic acid mixture (0.8/8/1.2 v/v). The pure fractions are lyophilized and the solid obtained is redissolved in 100 ml of water. The solution obtained is washed three times with ethyl acetate and then lyophilized to give 3.0 g of the expected product in the form of an amorphous white solid (yield=70%).

[α]$_D^{23}$=+1.3° (c=1.00; CH$_3$OH).

$^1$HMR (DMSO-d$_6$): 1.18 (d, 3H); 1.2–1.6 (m, 12H); 1.65–1.85 (m, 1H); 1.85–2.0 (m, 1H); 2.10 (t, 2H); 2.85–3.1 (m, 8H); 3.2–3.4 (m, 1H); 3.65 (d, 2H); 6.9–8.5 (m, 12H).

$^{13}$C NMR (D$_2$O/dioxane-h$_8$): 18.02; 23.68; 25.81; 26.31; 26.37; 28.51; 28.61; 31.23; 36.19; 39.22; 41.89; 43.44; 44.61; 46.10; 48.16; 158.20; 172.37; 178.71.

EXAMPLE 2

N-[2-[[4-[(3-(R,S)-Aminobutyl)amino]butyl]amino]-2-oxoethyl]-7-[(aminoiminomethyl)amino] heptanamide Tris(trifluoroacetate)

The expected product is obtained in the form of an amorphous white solid by following a procedure analogous to the synthesis scheme employed for Example 1, but using [3-[(4-aminobutyl)phenylmethyl)amino]-1-(R,S)-methylpropyl]carbamic acid, 1,1-dimethylethyl ester.

$^1$HNMR(DMSO-d$_6$): 1.18 (d, 3H); 1.2–1.35 (m, 4H); 1.4–1.60 (m, 8H); 1.65–1.85 (m, 1H); 1.85–2.0 (m, 1H); 2.10 (t, 2H); 2.8–3.2 (m, 8H); 3.2–3.4 (m, 1H); 3.65 (d, 2H); 6.8–8.7 (m, 12H).

$^{13}$C NMR (D$_2$O+dioxane-h$_8$): 18.01; 23.68; 25.81; 26.31; 26.37; 28.51; 28.60; 31.23; 36.18; 39.21; 41.88; 43.44; 44.61; 46.03; 48.16; 157.54; 172.38; 178.72.

PREPARATION VII

[3-[(3-Cyanopropyl)amino]-1-(R)-methylpropyl] carbamic Acid, 1,1-dimethylethyl ester 21 g (60.8.10$^{-3}$ mol) of [3-[(3-cyanopropyl)(phenylmethyl)amino]-1-(R)-methylpropyl]carbamic acid, 1,1-dimethylethyl ester are dissolved in 400 ml of ethanol, and 0.25 ml of 10M hydrochloric acid is then added, followed by 1.2 g of 5% palladium on charcoal. The mixture is stirred under a hydrogen atmosphere at room temperature and at atmospheric pressure. After a reaction time of 24 hours, the catalyst is filtered off and the filtrate is then concentrated under reduced pressure. The residue is purified by chromatography on silica gel using an ethyl acetate/ethanol/aqueous ammonia mixture (6/3/0.1 v/v) as the eluent to give 6 g of the expected product in the form of an oil (yield=34%).

$^1$H NMR (CDCl$_3$): 1.15 (d, 3H); 1.3–1.9 (m, 13H); 2.4–2.7 (m, 6H); 3.4–3.85 (m, 1H); 4.7–4.9 (bs, 1H).

PREPARATION VIII

[3-[(3-Cyanopropyl)[(1,1-dimethylethoxy)carbonyl]amino]-1-(R)-methylpropyl]carbamic Acid, 1,1-dimethylethyl Ester A solution of 5.82 g (22.92.10$^{-3}$ mol) of the compound obtained according to Preparation VII in 100 ml of tetrahydrofuran is prepared and 3.45 g (34.23.10$^{-3}$ mol) of triethylamine and then 5.97 g (27.38.10$^{-3}$ mol) of di(tert-butyl) dicarbonate [chemical structure: O[CO$_2$C(CH$_3$)$_3$]$_2$] are added. The reaction mixture is stirred for 15 h at room temperature. After concentration of the reaction medium under reduced pressure, the crude product is purified by chromatography on silica gel using a methylcyclohexane/ethyl acetate mixture (9/1 then 8/2 v/v) as the eluent to give 5.6 g of the expected product in the form of an oil (yield=68%).

$^1$H NMR (CDCl$_3$): 1.15 (d, 3H); 1.4–1.6 (m, 20H); 1.8–1.95 (m, 2H); 2.35 (t, 2H); 3.1–3.4 (m, 4H); 3.55–3.70 (m, 1H); 4.25–4.55 (bs, 1H).

PREPARATION IX

[3-[(4-Aminobutyl)[(1,1-dimethylethoxy)carbonyl]amino]-1-(R)-methylpropyl]carbamic Acid, 1,1-dimethylethyl Ester 5.5 g (15.5.10$^{-3}$ mol) of the compound obtained according to Preparation VIII are dissolved in 100 ml of methanol, 400 mg of Raney nickel are added and the mixture is stirred under a hydrogen atmosphere at room temperature under a pressure of 3.10$^5$ Pa for 24 h. The reaction mixture is subsequently filtered to remove the catalyst and then concentrated under reduced pressure. The residue is purified by chromatography on silica gel using a methylcyclohexane/ethyl acetate mixture (6/4 v/v) and then an ethyl acetate/ethanol/aqueous ammonia mixture (6/3/0.2 v/v) as the eluent to give 3.96 g of the expected product in the form of an oil (yield=71%).

$[\alpha]_D^{22}$=+41.3° (c=3; CHCl$_3$).

$^1$H NMR (CDCl$_3$): 1.15 (d, 3H); 1.4–1.7 (m, 22H); 1.8 (s, 4H); 2.75 (t, 2H); 3.05–3.35 (m, 4H); 3.55–3.7 (m, 1H); 4.35–4.6 (bs, 1H).

PREPARATION X

3-[[(1,1-Dimethylethoxy)carbonyl]amino]-13-(carboxy)-15,15,16,16-tetramethyl-11-oxo-14-oxa-2,4,12-triaza-15-silaheptadec-2-enoic Acid, 1,1-dimethylethyl Ester 1.73 g (2.94.10$^{-3}$ mol) of 3-[[(1,1-dimethylethoxy)carbonyl]amino]-13-(methoxycarbonyl)-15,15,16,16-tetramethyl-11-oxo-14-oxa-2,4,12-triaza-15-silaheptadec-2-enoic acid, 1,1-dimethylethyl ester are dissolved in 4 ml of 1,2-dimethoxyethane, and 4 ml of molar aqueous sodium hydroxide solution are added. The reaction mixture is stirred for 10 minutes at room temperature, 20 ml of water and 20 ml of dichloromethane are then added and the mixture is acidified to pH 2 with 1N hydrochloric acid, with thorough stirring. After separation of the organic phase, the aqueous phase is extracted with 3 times 25 ml of dichloromethane. The combined organic phases are dried over magnesium sulfate and then concentrated under reduced pressure to give 1.68 g of the expected product in the form of a colorless oil (quantitative yield).

$^1$H NMR (CDCl$_3$): 0.1–0.15 (m, 6H); 0.85–1 (m, 9H); 1.3–1.8 (m, 26H); 2.25 (t, 2H); 3.2–3.45 (m, 2H); 5.55 (d, 1H); 7.0–7.1 (bs, 1H); 8.3–8.7 (m, 1H); 11–12 (bs, 1H).

PREPARATION XI

3-[[(1,1-Dimethylethoxy)carbonyl]amino]-20-[(1,1-dimethylethoxy)carbonyl]-23-(R)-methyl-13-[[(1,1-dimethylethyl)dimethylsilyl]oxy]-11,14-dioxo-2,4,12,15,20,24-hexaazapentacos-2-enedioic acid, bis(1,1-dimethylethyl) ester 1.68 g (2.92.10$^{-3}$ mol) of the product obtained according to Preparation X are dissolved in 30 ml of dichloromethane and the solution is cooled to 0° C. 0.4 g (3.10$^{-3}$ mol) of HOBT and then 1.24 g (6.10$^{-3}$ mol) of DCC are added. This mixture is stirred for 15 minutes, 1.05 g (2.92.10$^{-3}$ mol) of the compound obtained according to Preparation IX are then added and the reaction medium is stirred at room temperature for 48 hours. The solvent is then removed under reduced presure and the residue is purified by chromatography on silica gel using an ethyl acetate/methylcyclohexane mixture (1/1 v/v) and then ethyl acetate as the eluent to give 0.78 g of the expected product in the form of an amorphous solid (yield=30%).

$[\alpha]_D^{19.5}$=−0.1° (c=1; CHCl$_3$).

$^1$H NMR (DMSO-d$_6$): 0.079 (s, 3H); 0.137 (s, 3H); 0.88 (s, 9H); 1.05 (d, 3H); 1.1–1.95 (m, 50H); 2.14 (t, 2H); 3–3.4 (m, 9H); 5.60 (d, 1H); 6.7 (bs, 1H); 7.75–7.85 (bs, 1H); 8.3 (t, 1H); 8.62 (d, 1H); 11.5 (s, 1H).

EXAMPLE 3

N-[2-[[4-[(3-(R)-Aminobutyl)amino]butyl]amino]-1-(R,S)-methoxy-2-oxoethyl]-7-[(aminoiminomethyl)amino]heptanamide tris(trifluoroacetate)

31 mg (38.7.10$^{-6}$ mol) of the compound obtained according to Preparation XI are dissolved in 10 ml of trifluoroacetic acid and 1 ml of methanol. This mixture is subsequently stirred for 4 hours and the solvent is then removed under reduced pressure at room temperature. The crude product is then purified by chromatography on grafted silica [of the RP18 type (particle size: 5 to 20 μm)] using an acetonitrile/water/trifluoroacetic acid mixture (1.5/8/0.5 then 2/8/0.1 v/v) as the eluent to give 16 mg of the expected product in the form of an amorphous white solid (yield=55%).

$[\alpha]_D^{20}$=+1.20 (c=1.53; H$_2$O).

$^1$H NMR (DMSO-d$_6$): 1.18 (d, 3H); 1.2–1.35 (m, 4H); 1.35–1.65 (m, 8); 1.65–1.85 (m, 1H); 1.85–2.0 (m, 1H); 2.1–2.3 (m, 2H); 2.8–3.2 (m, 8H); 3.22 (m, 4H); 5.26 (d, 1H); 6.8–7.4 (bs, 3H); 7.55 (t, 1H); 7.8–8.05 (m, 4H); 8.15 (t, 1H); 8.48 (d, 1H); 8.5–8.65 (m, 2H).

EXAMPLE 4

7-[(Aminoiminomethyl)amino]-N-[2-[[4-[(3-(R)-aminobutyl)amino]butyl]-amino]-1-(R,S)-hydroxy-2-oxoethyl]ethyl]heptanamide tris(trifluoroacetate)

150 mg (0.164.10$^{-3}$ mol) of the compound obtained according to Preparation XI are dissolved in 4 ml of trifluoroacetic acid and the solution is stirred at room temperature for 4 hours. After removal of the solvent under reduced pressure, the product is purified by the FPLC (Fast Protein Liquid Chromatography) technique on a gel of the C.M. SEPHAROSE® FAST FLOW type (Pharmacia) using, as the eluent, pure water and then sodium chloride solution whose concentration increases gradually from 0 to 1M with a substantially linear gradient and a concentration plateau at 0.4M. The fractions containing the expected product are lyophilized and the white solid obtained is desalinated by chromatography on a column of SEPHADEX® LH20 (Pharmacia) using methanol as the eluent. The final purification of the product is effected by chromatography on grafted silica gel of the RP18 type ("Varian Bond Elut") using pure water and then an acetonitrile/water/trifluoroacetic acid mixture (7/0.5/0.2 v/v) as the eluent to give 10 mg of the expected product in the form of an amorphous white solid.

$[\alpha]_D^{22}$=+1.50 (c=0.45; $CH_3OH$).

$^1$H NMR (D2O): 1.25–1.4 (m, 7H); 1.45–1.8 (m, 8H); 1.85–2.05 (m, 1H); 2.1–2.20 (m, 1H); 2.25 (t, 2H); 3.0–3.3 (m, 8H); 3.4–3.55 (m, 1H); 5.41 (s, 1H).

$^{13}$C NMR ($H_2O$+dioxane-$h_8$): 18.34; 23.70; 25.6; 26.12; 26.22; 28.38; 28.51; 31.14; 36.33; 39.37; 41.94; 44.66; 46.28; 48.22; 72.54; 157.25; 171.79; 178.41.

PREPARATION XII

3-[[(1,1-Dimethylethoxy)carbonyl]amino]-23-(R,S)-methyl-20-(phenylmethyl)-13-[[(1,1-dimethylethyl)dimethylsilyl]oxy]-11,14-dioxo-2,4,12,15,20,24-hexaazapentacos-2-enedioic acid, bis(1,1-dimethylethyl) ester The expected product is obtained in the form of an oil with a yield of 49% by following a procedure analogous to the method of Preparation XI, but using [3-[(4-aminobutyl)(phenylmethyl)amino]-1-(R,S)-methylpropyl]carbamic acid, 1,1-dimethylethyl ester.

$^1$H NMR ($CDCl_3$): 0.105 (s, 3H); 0.21 (s, 3H); 0.90 (s, 9H); 1.04 (d, 3H); 1.3–1.7 (m, 41H); 2.20 (m, 2H); 2.41 (m, 2H); 2.55 (m, 1H); 3.1–3.75 (m, 7H); 5.3 (bs, 1H); 5.7 (d, 1H); 6.4 (bs, 1H); 6.7 (bs, 1H); 7.20–7.30 (m, 5H); 8.3 (bs, 1H); 11.5 (s, 1H).

PREPARATION XIII

3-[[(1,1-Dimethylethoxy)carbonyl]amino]-23-(R,S)-methyl-13-(R,S)-[[(1,1-dimethylethyl)dimethylsilyl]oxy]-11,14-dioxo-2,4,12,15,20,24-hexaazapentacos-2-enedioic acid, bis(1,1-dimethylethyl) ester 300 mg ($0.33.10^{-3}$ mol) of the compound obtained according to Preparation XII are dissolved in 30 ml of methanol, and 30 mg of palladium hydroxide are added. The mixture is stirred under a hydrogen atmosphere at atmospheric pressure and at room temperature for 15 min and the catalyst is then filtered off. After concentration, the crude product is purified by chromatography on silica gel using an ethyl acetate/ethanol/aqueous ammonia mixture (6/3/0.1 v/v) as the eluent to give 200 mg of the expected product in the form of an oil (yield=74%).

$^1$H NMR ($CDCl_3$): 0.011 (s, 3H); 0.021 (s, 3H); 0.9 (s, 9H); 1.13 (d, 3H); 1.3–1.9 (m, 41H); 2.20 (m, 2H); 2.7 (m, 4H); 3.1–3.6 (m, 5H); 4.2–4.4 (bs, 1H); 4.8 (bs, 1H); 5.7 (d, 1H); 6.7–6.9 (m, 2H); 8.3 (bs, 1H); 11.5 (s, 1H).

EXAMPLE 5

N-[2-[[4-[(3-(R,S)-Aminobuytl)amino]butyl]amino]-1-(R,S)-hydroxy-2-oxoethyl]-7-[(aminoiminomethyl)amino]heptanamide tris (trifluoroacetate)

200 mg ($0.245.10^{-3}$ mol) of the compound obtained according to Preparation XIII are stirred in 10 ml of trifluoroacetic acid at room temperature for 45 minutes. After evaporation of the solvent, the compound is purified by chromatography on grafted silica gel of the RP18 5-20N type using an acetonitrile/water/trifluoroacetic acid mixture (2/8/0.1 v/v) as the eluent. After lyophilization, 82 mg of the expected product are obtained in the form of a white solid (yield=45%).

$^1$H NMR (DMSO): 1.15 (d, 3H); 1.2–1.35 (m, 4H); 1.35–1.55 (m, 8H); 1.65–1.8 (m, 1H); 1.85–2.0 (m, 1H); 2.1–2.2 (t, 2H); 2.85–3.35 (m, 9H); 5.4 (d, 1H); 6.5 (bs, 1H); 6.7–7.4 (bs, 3H); 7.6 (t, 1H); 7.8–8.1 (m, 5H); 8.4–8.7 (m, 3H).

PREPARATION XIV 13-(S)-[[(9H-Fluoren-9-yl)methoxycarbonyl]amino]-3-(R)-methyl-12-oxo-14-(phenylmethoxy)-6-(phenylmethyl)-2,6,11-triazatetradecanoic acid, 1,1-dimethylethyl ester 1.71 g ($4.1.10^{-3}$ mol) of N-[(9H-fluoren-9-yl)methoxycarbonyl]-O-phenylmethyl-(L)-serine are dissolved in 60 ml of dichloromethane. The solution is cooled to 0° C. and a solution of 0.55 g ($4.10^{-3}$ mol) of HOBT and 1.54 g ($7.5.10^{-3}$ mol) of DCC in 20 ml of dichloromethane is added. The mixture is stirred for 0.5 hour, 1.30 g ($3.72.10^{-3}$ mol) of N-[3-[(4-aminobutyl)(phenylmethyl)amino]-1-(R)-methylpropyl]carbamic acid, 1, 1-dimethylethyl ester are then added and the reaction mixture is stirred at room temperature for 16 hours. The solvent is removed under reduced pressure and the residue is purified by chromatography on silica gel using an ethyl acetate/methylcyclohexane mixture (1/1 v/v) and then pure ethyl acetate as the eluent to give 2.7 g of the expected product in the form of a white crystalline solid (yield=96%).

$[\alpha]_D^{23}$=+11° (c=1.1; $CHCl_3$).

M.p.=118° C.

$^1$H NMR ($CDCl_3$): 1.02 (d, 3H); 1.3–1.8 (m, 15H); 2.25–2.6 (m, 4H); 3.15–3.3 (m, 2H); 3.35–3.75 (m, 4H); 3.8–3.95 (m, 1H); 4.15–4.6 (m, 6H); 5.3 (d, 1H); 5.6–5.8 (bs, 1H); 6.35–6.55 (bs, 1H); 7.15–7.45 (m, 14H); 7.55 (d, 2H); 7.75 (d, 2H).

PREPARATION XV 13-(S)-Amino-3-(R)-methyl-12-oxo-14-phenylmethoxy-6-phenylmethyl-2,6,11-triazatetradecanoic acid, 1,1-dimethylethyl ester 2.56 g ($3.42.10^{-3}$ mol) of the compound obtained according to Preparation XIV are dissolved in 100 ml of dichloromethane, and 5 g of piperidine are added. The mixture is stirred for 3 hours at room temperature and then concentrated under reduced pressure. When concentration is complete, 2 times 10 ml of toluene are added to drive off the excess piperidine. The residue is then purified by chromatography on silica gel using an ethyl acetate/methanol mixture (8/2 v/v) as the eluent to give 1.68 g of the expected product in the form of a viscous yellow oil (yield=90%).

$[\alpha]_D^{22}$=+10° (c=1.1; $CHCl_3$).

$^1$H NMR ($CDCl_3$): 1.03 (d, 3H); 1.4–1.7 (m, 15H); 2.3–2.65 (m, 4H); 3.15–3.30 (m, 2H); 3.4–3.8 (m, 6H); 4.5 (s, 2H); 5.35–5.55 (bs, 1H); 7.2–7.5 (m, 10H) [(amine and amide protons not detected)].

PREPARATION XVI

3-[[(1,1-Dimethylethoxy)carbonyl]amino]-13-(S)-[phenylmethoxymethyl]-23-(R)-methyl-20-phenylmethyl-11,14-dioxo-2,4,12,15,20,24-hexaazapentacos-2-enedioic acid, bis(1,1-dimethylethyl) ester 1.46 g ($3.79.10^{-3}$ mol) of the compound obtained in Preparation II and 60 ml of dichloromethane are mixed and then cooled to 0° C. A solution of 0.51 g (3.79.10$^{-3}$ mol) of HOBT and 1.56 g (7.56.10$^{-3}$ mol) of DCC in 20 ml of dichloromethane is added. After stirring for 30 minutes, 1.60 g (3.10$^{-3}$ mol) of the compound obtained according to Preparation XV are added and the reaction mixture is stirred for 16 hours at room temperature. It is then concentrated under reduced pressure and purified by chromatography on silica gel using an ethyl acetate/methylcyclohexane mixture (6/4 v/v) and then pure ethyl acetate as the eluent to give 2.27 g of the expected product in the form of an oil (yield=83%).
$[\alpha]_D^{22}$=+4.2° (c=4.7; CHCl$_3$).
$^1$H NMR (CDCl$_3$): 1.03 (d, 3H); 1.2–1.8 (m, 41H); 2.2 (t, 2H); 2.3–2.65 (m, 4H); 3.1–3.8 (m, 8H); 3.85 (dd, 1H); 4.55 (q, 3H); 5.3–5.4 (m, 1H); 6.3–6.6 (m, 2H); 7.2–7.4 (m, 10H); 8.3 (t, 1H); 11.5 (s, 1H).

PREPARATION XVII

3-[[(1,1-Dimethylethoxy)carbonyl]amino]-13-(S)-[phenylmethoxymethyl]-23-(R)-methyl-11,14-dioxo-2,4,12,15,20,24-hexaazapentacos-2-enedioic acid, bis(1,1-dimethylethyl) ester A solution of 1.65 g (1.84.10$^{-3}$ mol) of the compound obtained according to Preparation XVI in 100 ml of ethanol is prepared. 200 mg of 10% palladium on charcoal are added and this reaction mixture is stirred under a hydrogen atmosphere at atmospheric pressure for 24 hours at room temperature. The catalyst is filtered off and the filtrate is concentrated under reduced pressure. The residue is purified by chromatography on silica gel using an ethyl acetate/ethanol/aqueous ammonia mixture (6/3/0.1 v/v) as the eluent to give 1 g of the expected product in the form of a viscous yellow oil (yield=67%).
$^1$H NMR (CDCl$_3$): 1.15 (d, 3H); 1.3–1.9 (m, 41H); 2.2 (t, 2H); 2.5–2.7 (m, 4H); 3.2–3.3 (m, 2H); 3.4 (td, 2H); 3.5 (t, 1H); 3.65–3.75 (t, 1H); 3.85 (m, 1H); 4.45–4.65 (m, 3H); 4.8–4.9 (bs, 1H); 6.4–6.5 (bs, 1H); 6.45 (t, 1H); 7.25–7.4 (m, 5H); 8.3 (t, 1H); 11.5 (s, 1H).

PREPARATION XVIII

3-[[(1,1-Dimethylethoxy)carbonyl] amino]-13-(S)-(hydroxymethyl)-23-(R)-methyl-11,14-dioxo-2,4,12,15,20,24-hexaazapentacos-2-enedioic acid, bis(1,1-dimethylethyl) ester The expected product is obtained with a yield of 95% by following a procedure analogous to Preparation XVII, starting from the compound obtained according to Preparation XVII but carrying out the hydrogenation on a reaction medium acidified to pH 3.5 with concentrated hydrochloric acid.
$[\alpha]_D^{22}$=−5.6° (c=1.0; CHCl$_3$).
$^1$H NMR (CDCl$_3$): 1.2 (d, 3H); 1.3–2.0 (m, 41H); 2.35 (t, 2H); 2.8–3.55 (m, 9H); 3.7–3.9 (m, 2H); 4.0–4.1 (m, 1H); 4.85–4.95 (bs, 1H); 7.35 (t, 1H); 7.4 (d, 1H); 8.3 (t, 1H); 8.6–8.8 (bs, 1H); 9.3–9.5 (bs, 1H); 11.5 (s, 1H).

EXAMPLE 6

N-[2-[[4-[(3-(R)-Aminobutyl)amino]butyl]amino]-1-(S)-hydroxymethyl-2-oxoethyl]-7-[(aminoiminomethyl)amino]heptanamide tris (trifluoroacetate)

A solution of 1.10 g (1.54. 10$^{-3}$ mol) of the compound obtained according to Preparation XVIII in 15 ml of dichloromethane is prepared, 15 ml of trifluoroacetic acid are added and the reaction medium is stirred for 16 hours at room temperature. It is then concentrated under reduced pressure and purified by chromatography on grafted silica gel of the RP18 type using a water/trifluoroacetic acid/acetonitrile mixture (8/1/1 v/v) as the eluent. The fractions containing the desired pure product are lyophilized and then taken up with 100 ml of distilled water, extracted with ethyl acetate and lyophilized again to give 610 mg of the expected product in the form of an amorphous white solid (yield= 52%).
$[\alpha]_D^{22}$=−3.2° (c=1.0; CH$_3$OH).
$^1$H NMR (DMSO-d$_6$): 1.2 (d, 3H); 1.2–1.35 (m, 4H); 1.4–1.6 (m, 8H); 1.70–1.85 (m, 1H); 1.85–2.0 (m, 1H); 2.14 (t, 2H); 2.85–3.15 (m, 8H); 3.25–3.4 (m, 1H); 3.55 (d, 2H); 4.2 (q, 1H ); 4.8–4.95 (bs, 1H); 6.85–7.4 (bs, 3H); 7.65 (t, 1H); 7.80 (d, 1H); 7.9 (t, 1H); 7.95–8.1 (m, 3H); 8.5–8.8 (bs, 3H).
$^{13}$C NMR (D$_2$O+dioxane-h$_8$): 17.77; 23.43; 25.58; 26.06; 26.09; 28.25; 28.35; 30.97; 35.86; 39.06; 41.65; 44.35; 45.81; 47.90; 56.54; 61.65; 158.00; 172.54; 178.1.

PREPARATION XIX

7-Bromoheptanamide

A mixture of 25 g (0.131 mol) of 7-bromoheptanenitrile and 100 ml of concentrated hydrochloric acid (d=1.19) is prepared and stirred for 12 hours at room temperature (advantageously at 15°–20° C.). This mixture is then poured onto 300 g of ice and the white precipitate obtained is then filtered off. After washing with water and drying, the crude product is recrystallized from an ethyl acetate/methylcyclohexane mixture to give 26.2 g of the expected product in the form of white crystals (yield=95%).
M.p.=84° C.

PREPARATION XX

7-Azidoheptanamide 16.4 g (0.25 mol) of sodium nitride are added to a solution of 26.2 g (0.126 mol) of 7-bromoheptanamide in 150 ml of DMSO. After stirring for 3.5 hours at 80° C., the reaction mixture is poured into water and extracted with ethyl acetate. The organic phase is washed with sodium chloride solution and then dried and concentrated under reduced pressure. The solid obtained is recrystallized from an ethyl acetate/isopropyl ether mixture to give 14 g of the expected product in the form of a white crystalline solid (yield=65%).
M.p.=62° C.

PREPARATION XXI

2-[(7-Azido-1-oxoheptyl)amino]-2-[1-(S)-(naphthalen-2-yl)ethoxy]acetic acid, methyl ester A mixture of 4.4 g (26.1.10$^{-3}$ mol) of 7-azidoheptanamide, 2.9 ml (29.2.10$^{-3}$ mol) of methyl 2-hydroxy-2-methoxyacetate and 250 ml of dichloromethane is prepared and refluxed for 24 hours by means of a device which is such that the reflux condensate passes through a bed of 4 Å molecular sieves (about 30 g). After return to room temperature, the device for eliminating the methanol is removed and 2.29 ml (31.10$^{-3}$ mol) of thionyl chloride are added to the reaction medium, which is then refluxed again for 1.75 h. The reaction mixture is subsequently concentrated under reduced pressure and then taken up with 50 ml of dichloromethane. A solution of 2.29 ml (31.10⁻³ mol) of triethylamine and 4.5 g (26.10⁻³ mol) of (S)-(−)-α-methyl-2-naphthalenemethanol [or 1-(S)-(naphthalen-2-yl)ethanol] in 50 ml of dichloromethane is added. The reaction mixture is stirred for 24 hours at room temperature and then washed successively with 100 ml of 1N hydrochloric acid and sodium chloride solution. After drying, the organic phase is concentrated under reduced pressure and the residue is purified by chromatography on silica gel using a hexane/2-propanol mixture (9/1 v/v) as the eluent to give 6.67 g of the expected product in the form of a colorless oil (yield=62%).
$[\alpha]_D^{25}$=−68° (c=1.16; $CHCl_3$).
¹H NMR ($CDCl_3$): 1.05–1.67 (m, 8H); 1.52 (d, 3Hy); 1.58 (d, 3Hx); 1.73–1.9 (2m, 2Hy); 2.28 (dd, 2Hx); 3.17 (t, 2Hy); 3.27 (t, 2Hx); 3.68 (s, 3Hx); 3.8 (s, 3Hy); 4.96 (m, 1H); 5.55 (d, 1Hx); 5.86 (d, 1Hy); 6.18 (d, 1Hy); 6.55 (d, 1Hx); 7.4–7.5 (m, 3H); 7.8–7.9 (m, 4H).
(The protons denoted by Hx and Hy can be assigned to the x and y epimers, respectively, of the compound analyzed.)

PREPARATION XXII 3-(R)-Methyl-6-phenylmethyl-12-oxo-13,13,13-trifluoro-2,6,11-triazatridecanoic acid, 1,1-dimethylethyl ester A solution of 3.12 g (8.9.10⁻³ mol) of [1-(R)-methyl-3-[(phenylmethyl)(4-aminobutyl)amino]propyl]carbamic acid, 1,1-dimethylethyl ester and 1.37 ml (9.8.10⁻³ mol) of triethylamine in 20 ml of dichloromethane is prepared and a solution of 1.39 ml (9.84.10⁻³ mol) of trifluoroacetic anhydride in 10 ml of dichloromethane is added dropwise, the temperature of the reaction medium being kept at 0° C. The mixture is subsequently stirred for 1.5 h at about 20° C. and then washed successively with 1N hydrochloric acid solution, sodium bicarbonate solution and water. The organic phase is dried and concentrated under reduced pressure. The residue obtained is purified by chromatography on silica gel using an ethyl acetate/methylcyclohexane mixture (1/1 v/v) as the eluent to give 2.6 g of the expected product in the form of a hygroscopic white solid (yield=65%).
$[\alpha]_D^{22}$=0° (c=1; $CH_3OH$).
¹H NMR (DMSO-d₆): 0.94 (d, 3H); 1.35–1.56 (m, 15H); 2.31–2.37 (m, 4H); 3.11 (m, 2H); 3.47 (m, 3H); 7.19–7.29 (m, 5H); 9.38 (t, 1H).

PREPARATION XXIII

N-[4-[(3-(R)-Aminobutyl)(phenylmethyl)amino]butyl]-2,2,2-trifluoroacetamide (dihydrochloride)

A mixture of 2.8 g (6.8.10⁻³ mol) of the compound obtained according to Preparation XXII and 32 ml of a 1M solution of hydrogen chloride in ethyl acetate is prepared and the resulting solution is stirred for 24 h at room temperature. The reaction medium is then concentrated under reduced pressure to give 2.34 g of the expected product in the form of a hygroscopic amorphous solid (yield=89%).
$[\alpha]_D^{22}$=+1.86° (c=1.04; $CH_3O$).
¹H NMR (DMSO-d₆): 1.14–1.18 (m, 3H); 1.4–1.5 (m, 2H); 1.7–1.8 (m, 2H); 1.9–2 (m, 1H); 2.1–2.2 (m, 1H); 3.13–3.48 (m, 7H); 4.32 (s, 2H); 7.47–7.48 (m, 3H); 7.6 (m, 2H); 8.1 (m, 3H); 9.5 (m, 1H); 10.7 (m, 1H).

PREPARATION XXIV

N-[4-[(3-(R)-Aminobutyl)amino]butyl]-2,2,2-trifluoroacetamide (dihydrochloride)

A solution of 2.34 g (5.56.10⁻³ mol) of the compound according to Preparation XXIII in 50 ml of methanol is prepared and 0.585 ml (6.67.10⁻³ mol) of concentrated hydrochloric acid and then 200 mg of 10% palladium on charcoal are added. The mixture is stirred under a hydrogen atmosphere at a pressure of 10⁵ Pa and at room temperature for 8 h. After separation of the catalyst by filtration, the filtrate is concentrated under reduced pressure to give 1.72 g of the expected product in the form of a white powder (yield=98%).
M.p.=210°–215° C.
$[\alpha]_D^{25}$=+2° (c=1.15; $CH_3OH$).

PREPARATION XXV 3-(R)-Methyl-6-(phenylmethoxycarbonyl)-12-oxo-13,13,13-trifluoromethyl-2,6,11-triazatridecanoic acid, phenylmethyl ester 1 g (2.32.10⁻³ mol) of the compound obtained according to Preparation XXIV is dissolved in 15 ml of methanol, and aqueous sodium bicarbonate solution is added dropwise until the pH is 9. The mixture is cooled to 0° C. and 1 ml of benzyl chloroformate (6.97.10⁻³ mol) is added. The pH is then kept at 9 by adding the sodium bicarbonate solution. When the pH is stable, the reaction medium is stirred for 2 h and then neutralized to pH 7 with dilute hydrochloric acid solution. The mixture is partially concentrated under reduced pressure to remove the methanol, and the residual aqueous phase is extracted with ethyl acetate. The organic phase obtained is washed with saturated sodium chloride solution, dried and then concentrated under reduced pressure. The residue obtained is purified by chromatography on silica gel using an ethyl acetate/methylcyclohexane mixture (1/1 v/v) as the eluent to give 0.88 g of the expected product in the form of a thick oil (yield=72%); this product is then crystallized from isopropyl ether.
M.p.=74° C.
$[\alpha]_D^{25}$=5° (c=0.98; $CHCl_3$).

PREPARATION XXVI

N-[4-Aminobutyl]-N-[3-(R)-[(phenylmethoxycarbonyl)amino]butyl]carbamic acid, phenylmethyl ester A solution of 0.92 g (1.75.10⁻³ mol) of the compound obtained according to Preparation XXV in 20 ml of 1,2-dimethoxyethane is prepared and 8.8 ml of 1N aqueous sodium hydroxide solution are added. The mixture is stirred for 2 hours at room temperature, 50 ml of saturated aqueous sodium chloride solution are then added and the mixture is extracted with ethyl acetate. The organic phase is dried and then concentrated under reduced pressure to give 0.75 g of the expected product in the form of a thick oil (yield=100%).
¹H NMR (DMSO-d₆): 1.03 (m, 3H); 1.2–1.25 and 1.43–1.46 (m, 2H); 1.59 (m, 2H); 3.17–3.47 (m, 6H); 3.48 (m, 1H); 5.0 (s, 2H); 5.05 (s, 2H); 7.22 (d, 1H); 7.25–7.5 (m, 10H).

PREPARATION XXVII

2-[(7-Azido-1-oxoheptyl)amino]-2-[1-(S)-(naphthalen-2-yl)ethoxy]acetic acid 4.75 g (11.5.10⁻³ mol) of the ester obtained according to Preparation XXI are dissolved in 50 ml of 1,2-dimethoxyethane, and 13.8 ml of 1N aqueous sodium hydroxide solution are added dropwise. The mixture is stirred for 1 h at room temperature and then acidified to pH 2 with 1N hydrochloric acid solution. 50 ml of saturated sodium chloride solution are added and the mixture is then extracted with ethyl acetate. The organic phase is dried and then concentrated under reduced pressure at room temperature to give 4.6 g of the expected product in the form of a thick oil (yield=99%).

$[\alpha]_D^{25}=-76°$ (c=0.96; CHCl$_3$).

$^1$H NMR (DMSO-d$_6$): 1.09–1.54 (m, 8H); 1.43 and 1.47 (2d, 3H); 2.18 (m, 2Ha); 2.50 (m, 2Hb); 3.24 (t, 2Ha); 3.31 (t, 2Hb); 4.8 (q, 1H); 5.25 (d, 1Ha); 5.49 (d, 1Hb); 7.45–7.55 (m, 3H); 7.79 (s, 1H); 7.85–7.93 (m, 3H); 8.72 (d, 1Hb); 8.80 (d, 1Hb); 13 (m, 1H).

PREPARATION XXVIII

21-Azido-13-(S)-[1-(S)-(naphthalen-2-yl)ethoxy]-6-(phenylmethoxycarbonyl)-3-(R)-methyl-12,15-dioxo-2,6,11,14-tetraazaheneicosanoic acid, phenylmethyl ester A solution of 4.58 g (11.5.10$^{-3}$ mol) of the acid obtained according to Preparation XXVII in 50 ml of dichloromethane is prepared and 1.55 g (11.5. 10$^{-3}$ mol) of HOBT and 2.6 g (12.6.10$^{-3}$ mol) of DCC are added. After stirring for 0.5 h at room temperature, 4.93 g (11.5.10$^{-3}$ mol) of the product obtained according to Preparation XXVI are added and the reaction mixture is stirred for 24 hours at room temperature. It is then concentrated under reduced pressure and the residue is taken up with 50 ml of ethyl acetate. The insoluble materials are filtered off and the filtrate is concentrated under reduced pressure. The resulting crude product containing the two isomers is purified by chromatography on silica gel ["Kieselgel 60 Merck" (particle size: 15 to 40 μm)] using an ethyl acetate/isopropyl ether mixture (7/3 v/v) as the eluent. This purification makes it possible to separate the two isomers (the expected product, in which the carbon in the 13-position is of (S) configuration, is eluted before its isomer, in which said carbon in the 13-position is of (R) configuration). This gives 3.7 g of the expected product in the form of a non-crystalline solid (yield=40%, i.e. 80% if one isomer is considered). 3.2 g of the second isomer are obtained simultaneously.

$[\alpha]_D^{25}=-41°$ (c=0.99; CHCl$_3$).

$^1$H NMR (DMSO-d$_6$): 1.04 (m, 3H); 1.42 (d, 3H); 1.28–1.6 (m, 14H); 2.1–2.2 (m, 2H); 3.0–3.17 (m, 6H); 3.31 (t, 2H); 3.49 (m, 1H); 4.8 (q, 1H); 4.99 (s, 2H); 5.04 (s, 2H); 5.17 (d, 1H); 7.2 (d, 1H); 7.22–7.32 (m, 10H); 7.48–7.57 (m, 3H); 7.8–7.9 (m, 4H); 8.0 (m, 1H); 8.64 (d, 1H).

PREPARATION XXVIII bis

21-Azido-13-(S)-[1-(S)-(naphthalen-2-yl)ethoxy]-6-(phenylmethoxycarbonyl)-3-(R,S)-methyl-12,15-dioxo-2,6,11,14-tetraazaheneicosanoic acid, phenylmethyl ester The expected product is obtained by following the method of Preparation XXVIII, replacing the product of Preparation XXVI with its racemate, namely N-[4-aminobutyl]-N-[3-(R, S)-[(phenylmethoxycarbonyl)amino]butyl]carbamic acid, phenylmethyl ester.

PREPARATION XXIX

3-[(Phenylmethoxycarbonyl)amino]-20-(phenylmethoxycarbonyl)-13-(S)-[1-(S)-(naphthalen-2-yl)ethoxy]-23-(R)-methyl-11,14-dioxo-2,4,12,15,20,24-hexaazapentacos-2-enedioic acid, bis(phenylmethyl) ester A solution of 3.55 g (4.47.10$^{-3}$ mol) of the compound obtained according to Preparation XXVIII in 50 ml of tetrahydrofuran is prepared and 1.41 g (5.36.10$^{-3}$ mol) of triphenylphosphine and 100 μl (5.36.10$^{-3}$ mol) of water are added. The mixture is heated at the reflux temperature of the solvent for 15 hours and then cooled to room temperature. 1.92 g (5.36. 10$^{-3}$ mol) of [[[(phenylmethoxy)carbonyl]amino](methylthio)methylene]carbamic acid, phenylmethyl ester (alternative name: N,N'-bis[benzyloxycarbonyl]-S-methylisothiourea) are then added and the mixture is stirred for 24 hours at room temperature. After concentration under reduced pressure, the residue is purified by chromatography on silica gel using ethyl acetate as the eluent. The purified product obtained is crystallized from ethyl ether and then recrystallized from a butanone/isopropyl ether mixture to give 2.5 g of the expected product in the form of a white powder (yield=52%).

M.p.=58° C.

$[\alpha]_D^{25}=-34°$ (c=1; CHCl$_3$).

PREPARATION XXIX bis

3-[(Phenylmethoxycarbonyl)amino]-20-(phenylmethoxycarbonyl)-13-(S)-[1-(S)-(naphthalen-2-yl)ethoxy]-23-(R,S)-methyl-11,14-dioxo-2,4,12,15,20,24-hexaazapentacos-2-enedioic acid, bis(phenylmethyl) ester The expected product is obtained by following the method of Preparation XXIX, replacing the product of Preparation XXVIII with that of Preparation XXVIII bis.

EXAMPLE 7

7-[(Aminoiminomethyl)amino]-N-[2-[[4-[(3-(R)-aminobutyl)amino]butyl]-amino]-1-(S)-hydroxy-2-oxoethyl]heptanamide (triacetate)

A solution of 130 mg (0.118.10$^{-3}$ mol) of the compound obtained according to Preparation XXIX in 3 ml of dioxane is prepared and then mixed with 50 ml of 1N aqueous acetic acid solution. 100 ml of Pearlman's catalyst (palladium hydroxide on charcoal containing about 20% of palladium) are subsequently added and the mixture is then stirred under a hydrogen atmosphere at a pressure of 20.10$^5$ Pa and at room temperature for about 30 hours. This operation is repeated once after the spent catalyst has been replaced with fresh catalyst. After separation of the catalyst by filtration, the filtrate is washed with 50 ml of ethyl ether and then lyophilized to give 40 mg of the expected compound in the form of a very hygroscopic white solid (yield=70%). The purity is greater than 99% (HPLC).

$[\alpha]_D^{20}=-11°$ [c=1.99; CH$_3$COOH(1N)H$_2$O)].

$^1$H NMR (D$_2$O): 1.26–1.28 (m, 7H); 1.4–1.7 (m, 8H); 1.8–2.0 (m, 1H); 3.0–3.12 (m, 6H); 3.22 (m, 2H); 3.41 (m, 1H); 5.37 (s, 1H).

$^{13}$C NMR (D$_2$O): 18.05; 23.73; 24.10; 25.66; 26.28; 28.48; 28.5; 31.2; 36.3; 39.3; 41.9; 44.6; 46.0; 48.15; 72.7; 157.5; 172.16; 178.3; 181.14.

EXAMPLE 8

7-[(Aminoiminomethyl)amino]-N-[2-[[4-[(3-(R,S)-aminobutyl)amino]butyl]-amino]-1-(S)-hydroxy-2-oxoethyl]heptanamide (triacetate)

The expected product is obtained by following the method of Example 7, replacing the product of Preparation XXIX with that of Preparation XXIX bis.

PREPARATION XXX

2-(S)-[(7-Azido-1-oxoheptyl)amino]-2-yl-(S)-(naphthalen-2-yl)ethoxylacetic acid, Methyl ester The mixture of isomers obtained according to Preparation XXI is separated by chromatography on silica gel

[AMICON Matrex phase, spherical silica Si 100-15s; pore size: 100 Å; particle size: 15 μm]. The eluent used is a dichloromethane/ethyl acetate mixture (95/5 v/v). 4.5 g of mixture yield 2.05 g of the expected compound (in crystalline form) together with 1.41 g of the (R) isomer and 1.04 g of a mixture of both isomers.
M.p.=32° C.
$[\alpha]_D^{30}$=−50° (c=0.94; CHCl$_3$).
$^1$H NMR (CDCl$_3$): 1.37–1.39 (m, 4H); 1.53 (d, 3H); 1.55–1.7 (m, 4H); 2.27 (d, 2H); 3.26 (t, 2H); 3.68 (s, 3H); 4.97 (q, 1H); 5.55 (d, 1H); 6.52 (d, 1H); 7.44–7.54 (m, 3H); 7.81–7.87 (m, 4H).

The absolute configuration of the carbon in the 2-position of this compound was verified by X-ray spectrography.

PREPARATION XXXI 2-(S)-[(7-Azido-1-oxoheptyl)amino]-2-[1-(S)-(naphthalen-2-yl)ethoxy]acetic acid The expected acid is obtained in the form of an oil with a yield of 100% by following a procedure analogous to the method of Preparation XXII, starting from the compound obtained according to Preparation XXX.
$[\alpha]_D^{25}$=−40° (c=1.1; CHCl$_3$).
$^1$H NMR (DMSO-d$_6$): 1.35–1.39 (m, 4H); 1.56 (d, 3H); 1.56–1.71 (m, 4H); 2.28 (t, 2H); 3.26 (t, 2H); 4.99 (q, 1H); 5.52 (d, 1H); 6.48 (d, 1H); 7.44–7.55 (m, 3H); 7.8–7.9 (m, 4H).

PREPARATION XXXII

21-Azido-13-(S)-[1-(S)-(naphthalen-2-yl)ethoxy]-6-(phenylmethoxycarbonyl)-3-(R)-methyl-12,15-dioxo-2,6,11,14-tetraazaheneicosanoic acid, phenylmethyl ester This product, which is identical to the compound of Preparation XXVIII, is obtained by the same method of synthesis as that described in Preparation XXVIII, except that purification by chromatography is not actually necessary in the present case.

Starting from the product of Preparation XXXII, the compound of Example 7 is obtained by following the operating procedures already described above (Preparation XXIX and Example 7).

PREPARATION XXXIII

2-[(7-Azido-1-oxoheptyl)amino]-2-(phenylmethoxy) acetic acid, methyl ester

The expected product is obtained in the form of a colorless oil (yield=67%) by following the method of Preparation XXI, but replacing the (S)-(−)-α-methyl-2-naphthalenemethanol with benzyl alcohol.
$^1$H NMR (CDCl$_3$): 1.3–1.5 (m, 4H); 1.5–1.75 (m, 4H); 2.25 (t, 2H); 3.25 (t, 2H); 3.8 (s, 3H); 4.71 (q, 2H); 5.73 (d, 1H); 6.50 (d, 1H); 7.25–7.45 (m, 5H).

PREPARATION XXXIV

2-[(7-Azido-1-oxoheptyl)amino]-2-(phenylmethoxy) acetic acid

The expected product is obtained by following the method of Preparation XXVII, but replacing the product of Preparation XXI with the product of Preparation XXXIII.
$^1$H NMR (CDCl$_3$): 1.3–1.5 (m, 4H); 1.55–1.75 (m, 4H); 2.26 (t, 2H); 3.25 (t, 2H); 4.7–4.8 (m, 2H); 5.75 (d, 1H); 6.59 (d, 1H); 7.25–7.4 (m, 5H) (m, 5H).

PREPARATION XXXIV

21-Azido-13-(R,S)-(phenylmethoxy)-6-(phenylmethoxycarbonyl)-3-(R)-methyl-12,15-dioxo-2,6,11,14-tetraazaheneicosanoic acid, phenylmethyl ester The expected product is obtained in the form of a yellow oil (yield=92%) by following the method of Preparation XXVIII, but replacing the product of Preparation XXVII with the product of Preparation XXXIV and without separating the isomers during the purification on silica gel.
$^1$H NMR (CDCl$_3$): 1.05–1.75 (m, 17H); 2.26 (t, 2H); 2.95–3.5 (m, 8H); 3.6–3.8 (m, 1H); 4.5–4.75 (m, 2H); 5.07 (s, 2H); 5.09 (s, 2H); 5.55–5.7 (m, 1H); 6.4–6.9 (m, 2H); 7.2–7.45 (m, 16H).

PREPARATION XXXVI

3-[(Phenylmethoxycarbonyl)amino]-20-(phenylmethoxycarbonyl)-13-(R,S)-(phenylmetboxy)-23-(R)-methyl-11,14-dioxo-2,4,12,15,20,24-hexaazapentacos-2-enedioic acid, bis (phenylmethyl) ester The expected product is obtained in the form of an amorphous solid (yield=69%) by following the method of Preparation XXIX, but replacing the product of Preparation XXVIII with the product of Preparation XXXV.
$^1$H NMR (CDCl$_3$): 0.95–1.1 (m, 3H); 1.2–1.7 (m, 14H); 2.1–2.25 (m, 2H); 3–3.4 (m, 8H); 3.4–3.55 (m, 1H); 4.49 (q, 2H); 4.99 (s, 2H); 5.02 (s, 2H); 5.03 (s, 2H); 5.20 (s, 2H); 5.46 (d, 1H); 7.15–7.5 (m, 26H); 8.12 (t, 1H); 8.39 (t, 1H); 8.63 (d, 1H); 11.59 (s, 1H).

EXAMPLE 4 bis

7-[(Aminoiminomethyl)amino]-N-[2-[[4-[(3-(R)-aminobutyl)amino]butyl]-amino]-1-(R,S)-hydroxy-2-oxoethyl]heptanamide triacetate The expected product is obtained in the form of an amorphous pale yellow solid (yield=81%) by following the method of Example 7, but replacing the product of Preparation XXIX with the product of Preparation XXXVI.
$[\alpha]_D^{21}$=+0.5° (c=1; MeOH).
$^1$H NMR (D$_2$O): 1.2–1.4 (m, 7H); 1.5–1.75 (m, 8H); 1.85 (s, 9H); 1.9–2.15 (m, 2H); 2.23 (m, 2H); 3–3.2 (m, 6H); 3.2–3.3 (m, 2H); 3.35–3.5 (m, 1H); 5.37 (s, 1H).
$^{13}$C NMR (D$_2$O): 18.05; 23.75; 24.10; 25.67; 26.30 (2C); 28.50; 28.55; 31.27; 36.30; 39.33; 41.88; 44.63; 46.07; 48.17; 72.76; 157.5; 172.16; 178.34; 181.14.

PREPARATION XXXVII

21-Azido-13-(S)-[1-(S)-(naphthalen-2-yl)ethoxy]-6-(phenylmethoxycarbonyl)-12,15-dioxo-2,6,11,14-tetraazaheneicosanoic acid, phenylmethyl ester The expected product is obtained with a yield of 30% [i.e. 60% when considering the S isomer] by following a procedure analogous to the method of Preparation XXVIII, starting from the compound obtained according to Preparation XXVII and [4-aminobutyl]-[3-[(phenylmethoxycarbonyl)amino]propyl]carbamic acid, phenylmethyl ester, after purification by chromatography on silica gel and elution with an ethyl acetate/isopropyl ether mixture (6/4 v/v).
$[\alpha]_D^{20}$=−40.70 (c=5.4; CHCl$_3$).
$^1$H NMR (DMSO-d$_6$): 1.44 (d, 3H); 1.2–1.6 (m, 14H); 2.17 (m, 2H); 2.9–3.05 (m, 6H); 3.31 (t, 2H); 4.8 (q, 1H); 4.99 (s, 2H); 5.04 (s, 2H); 5.17 (d, 1H); 7.27–7.32 (m, 11H); 7.81 (s, 1H)); 7.86–7.9 (m, 3H); 8.0 (m, 1H); 8.64 (d, 1H).

PREPARATION XXXVIII

3-[(Phenylmethoxycarbonyl)amino]-20-
(phenylmethoxycarbonyl)-13-(S)-[1-(S)-
(naphthalen-2-yl)ethoxy]-11,14-dioxo-2,4,12,15,20,
24-hexaazapentacos-2-enedioic acid, bis
(phenylmethyl) ester The expected product is obtained with a yield of 77% by following a procedure analogous to the method of Preparation XXIX, starting from the compound obtained according to Preparation XXXVII.
M.p.=98° C.
$[\alpha]_D^{25}=-33°$ (c=1; CHCl$_3$).

EXAMPLE 9

7-[(Aminoiminomethyl)amino]-N-[2-[[4-[(3-
aminopropyl)amino]butyl]amino]-1-(S)-hydroxy-2-
oxoethyl]heptanamide trihydrochloride The S isomer of 15-deoxyspergualin is obtained in the form of the triacetate by hydrogenating the compound of Preparation XXXVIII analogously to the method of Example 7; it is subsequently converted to the trihydrochloride with hydrochloric acid solution and then lyophilized. The physical characteristics of this product are identical to those published in the literature (J. Antibiot., 1987, 1316–1324).

The immunosuppressive activity of the products according to the invention was demonstrated by means of a test known as the graft-versus-host reaction. B6D2F1 male mice (C57B1/6×DBA/2 first generation hybrids) are immunosuppressed with an intraperitoneal (i.p.) injection of cyclophosphamide. Three days later (day 0 of the experiment: D0), they receive 4×10$^7$ C57B1/6 mouse splenocytes by intravenous administration. The animals are then divided up into groups of at least 8 and receive a daily treatment from D1 to D5 and from D7 to D10 by i.p. administration. The control group receives the vehicle only. The mortality is followed up to D60. The results, expressed as the mean survival value in days at the indicated dose, are collated in Table I, in which the values given are significant according to the Logrank test (probability less than or equal to 5%). For comparison, Table I also indicates the values obtained with products of related structure, namely:

in which *C is of (S) configuration.

The results in Table I show that the products of formula I and their non-toxic addition salts according to the invention have a better activity than the products of the prior art or require a lower posology to achieve an equivalent activity.

The products of formula I and their non-toxic addition salts according to the invention are useful in therapeutics as curative or preventive immunosuppressants in the context of the graft-versus-host reaction following a vascularized or non-vascularized graft, especially in preventing the rejection of vascular or non-vascular allogenic or xenogenic organs, in treating genetically defined or acquired autoimmune diseases (for example lupus erythematosus, multiple sclerosis, rheumatoid polyarthritis), in treating chronic inflammatory diseases, for example articular rheumatism, in treating or preventing hyperreactive inflammatory diseases, for example ulcerative colitis or asthma, as well as in any pathological condition where an immune disorder appears to be the cause or factor responsible for maintaining a degraded clinical state.

The products of formula I and their non-toxic addition salts according to the invention can also be administered in combination with cytotoxic anticancer drugs in order to limit their side effects, and in combination with the administration of products of biotechnological origin, especially recombinant cytokinins or monoclonal and polyclonal antibodies, in order to reduce the appearance of the protective antibodies produced by the patient.

The products of formula I and their non-toxic addition salts according to the invention can be used in the curative treatment of parasitosis, particularly in the case of malaria.

The products of formula I and their non-toxic addition salts according to the invention can be administered orally, by injection (especially intramuscular or intravenous injection), topically (especially in the form of a cream for local application, or eye drops), transdermally, rectally in the form of a suppository, or by inhalation.

The compounds of formula I and their addition salts are also useful as reagents for analytical assay, especially in pharmacology and particularly in the study of autoimmune diseases.

Best mode

The best mode (i.e. the preferred mode of carrying out the present invention) consists in using a compound of formula I in which R is OH, *C is of (R,S) or (S) configuration and **C is of (RS) or (R) configuration, or one of its non-toxic addition salts, as an immunosuppressant.

Product A:
15-deoxyspergualin (racemic compound in the form of the trihydrochloride)
Product B:

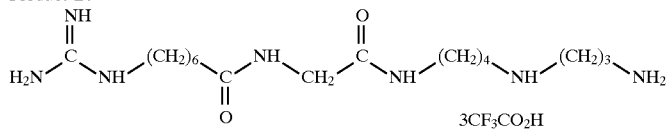

Product C:

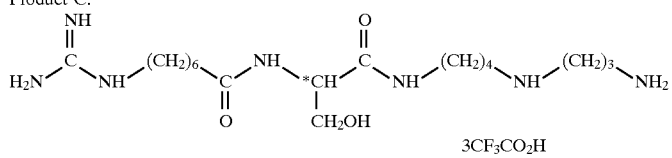

TABLE I

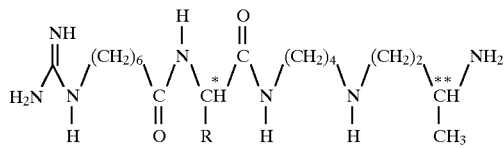

| EXAMPLE | R | *C | **C | Dose (mg/kg) | Activity |
|---|---|---|---|---|---|
| 1(a) | H | — | R | 1 | 57 |
| 2(a) | H | — | R, S | 1 | 42 |
| 3(a) | $OCH_3$ | R, S | R | 1 | 60 |
| 4(a) | OH | R, S | R | 0.1 | 55 |
| 4(a) | OH | R, S | R | 0.3 | 60 |
| 4(b) | OH | R, S | R | 0.2 | 60 |
| 5(a) | OH | R, S | R, S | 0.3 | 56 |
| 6(a) | $CH_2OH$ | S | R | 1 | 56 |
| 7(b) | OH | S | R | 0.1 | 60 |
| Product A | (See above) | | | 0.3 | 26 |
| Product B | (See above) | | | 1 | 27 |
| Product C | (See above) | | | 1 | 18 |

Notes
(a) tris(trifluoroacetate)
(b) triacetate

What is claimed is:

1. A compound belonging to the family of the 15-deoxyspergualin analogs, wherein said compound it is selected from the group consisting of:

(i) the compounds of the formula (I)

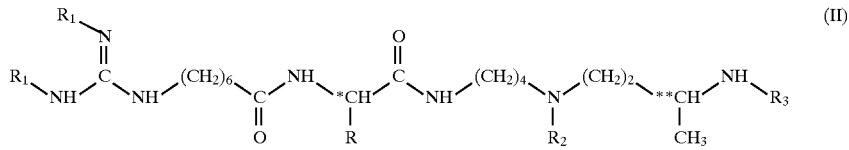

in which:

R is a hydrogen atom, a group OH, a group $OCH_3$ or a group $CH_2OH$,

*C, in the case where R is not a hydrogen atom, is an asymmetric carbon atom of (R,S), (R) or (S) configuration, and

**C is an asymmetric carbon atom of (R,S) or (R) configuration; and (ii) their addition salts.

2. A compound according to claim 1 wherein the asymmetric carbon atom **C is of (R) configuration.

3. A compound according to claim 1 wherein the asymmetric carbon atom *C is of (S) configuration and R is the group OH.

4. A method of preparing a compound of formula I or one of its addition salts according to claim 1, comprising the steps of:

(i) deprotecting a compound of formula II:

(II)

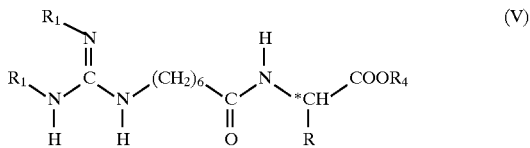

in which:

R is a hydrogen atom, a group $OCH_3$, a group OH, a group $CH_2OH$, a group OR' or a group $CH_2OR'$, R' is a protecting group for the hydroxyl group, $R_1$, $R_2$ and $R_3$, which are identical or different, are each a protecting group for the amine group,

*C, when R is not a hydrogen atom, is an asymmetric carbon atom of (R,S), (R) or (S) configuration, and

**C is an asymmetric carbon atom of (R,S) or (R) configuration, by one or more reaction treatments known to those skilled in the art, in order to replace all the protecting groups $R_1$, $R_2$, $R_3$ and R' with a hydrogen atom, and, if necessary, (ii) using an addition salt obtained according to step (i) to obtain the compound of formula I in the form of the free base by reaction with a strong base, and then using said free base to obtain the other addition salts.

5. A method according to claim 4 also comprising the steps of:

(a) according to variant A:

(i) condensing an acid of the formula (III)

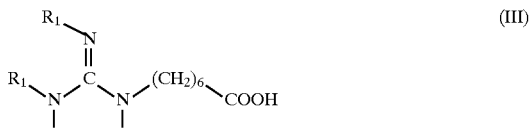

in which $R_1$ is an amino-protecting group, with an amino acid derivative of the formula (IV)

in which:

R is a hydrogen atom or a group $CH_2OR'$,

R' is a protecting group for the hydroxyl group, $R_4$ is a $C_1–C_3$-alkyl group, and

*C, when R is not the hydrogen atom, is an asymmetric carbon atom of (R,S), (R) or (S) configuration, by activating the acid group with a coupling agent of the carbodiimide type, in the presence of a nucleophilic agent, in an organic solvent, at a temperature between 0° and 40° C., at a rate of 1 mol of compound III to about 1 mol of compound IV, to give a compound of the formula (V)

in which R, $R_1$, $R_4$ and *C are as defined above;

(ii) hydrolyzing the ester group of a resulting compound of formula V, either according to step (i) above when R is the hydrogen atom or a group $CH_2OR'$ as described above, or by a known method when R is a group OR', where R' is a protecting group for the hydroxyl group, by reaction with a dilute base, in the presence of a water-miscible solvent, at a temperature around room temperature (5°–40° C.), for about 2 to 30 minutes, to give a compound of the formula $$
\begin{array}{c}
R_1 \\
\diagdown N \\
\parallel \\
R_1 \diagdown _{NH} \diagup C \diagdown _{NH} \diagup (CH_2)_6 \diagdown C \diagdown _{*CH} \diagup COOH \\
\quad\quad\quad\quad\quad\quad\quad\quad \parallel \quad\;\; | \\
\quad\quad\quad\quad\quad\quad\quad\quad O \quad\;\; R
\end{array}
\qquad (VI)
$$

in which $R_1$ and *C are as defined in the compound of formula V and R is a hydrogen atom, a group $CH_2OR'$ or a group $OR'$, $R'$ being a protecting group for the hydroxyl group; and (iii) reacting a resulting compound of formula VI with a compound of the formula $$
H_2N \diagup^{(CH_2)_4} \diagdown N \diagup^{(CH_2)_2} \diagdown {**CH} \diagup N \diagdown R_3
$$
(VII)

with $R_2$ below N and $CH_3$ below **CH.

in which:

$R_2$ and $R_3$, which are identical or different, are each an amino-protecting group, and

**C is an asymmetric carbon of (R,S) or (R) configuration, under conditions identical to those described in step (i) above, to give a compound of formula II:

(compound of formula II shown with $R_1$, $R_2$, $R_3$, R, *C, **C)

in which R, $R_1$, $R_2$, $R_3$, *C and **C are as defined above;

(b) according to variant B:
(i) condensing an amino acid derivative of the formula $$
R_5 \diagdown N \diagup *CH \diagdown COOH \\
\quad\quad\quad\; | \\
\quad\quad\quad\; R
$$
(VIII)

in which:

R is a hydrogen atom or a group $CH_2OR'$, where $R'$ is a protecting group for the hydroxyl group, $R_5$ is a protecting group for the amine group, and

*C, when R is not the hydrogen atom, is an asymmetric carbon atom of (R,S), (R) or (S) configuration, with a compound of the formula $$
H_2N \diagup^{(CH_2)_4} \diagdown N \diagup^{(CH_2)_2} \diagdown {**CH} \diagup N \diagdown R_3
$$
(VII)

in which:

$R_2$ and $R_3$, which are identical or different, are each an amino-protecting group, both being different from the protecting group $R_5$ present in the compound of formula VIII, and

**C is an asymmetric carbon atom of (R,S) or (R) configuration, under conditions analogous to those of the method of step (i) of variant A above, to give a compound of the formula (compound IX with $R_5$, R, $R_2$, $R_3$, CH₃, *C, **C)

in which R, $R_2$, $R_3$, $R_5$, *C and **C are as defined above;

(ii) deprotecting the resulting compound IX by a specific method for scission of the N—$R_5$ bond to give a compound of the formula (compound X)

in which R, $R_2$, $R_3$, *C and **C are as defined above; and (iii) condensing the resulting amine product of formula X with an acid of the formula $$
R_1 \diagdown N \\
\;\;\;\; \parallel \\
R_1 \diagdown _{NH} \diagup C \diagdown _{HN} \diagup (CH_2)_6 \diagdown COOH
$$
(III)

in which $R_1$ is an amino-protecting group, under operating conditions analogous to those described for method (i) of variant A, to give a compound of formula II:

(II)

in which R, $R_1$, $R_2$, $R_3$, *C and **C are as defined above;

(c) according to variant C:

($i_a$) reacting 7-azidoheptanade with methyl 2-hydroxy-2-methoxyacetate of the formula

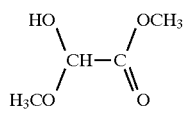

in a solvent of the halogenated hydrocarbon type, in the presence of a dehydrating, agent at a temperature between 25° C. and the reflux temperature of the solvent, for 10 to 50 hours, to give an intermediate of the formula

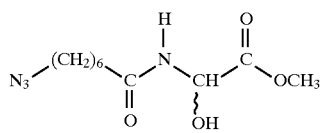
(XI)

($i_b$) reacting the resulting compound of formula XI in situ with thionyl chloride, at a temperature of about 40° C., for 1 to 3 hours, to give the halogenated compound of the formula

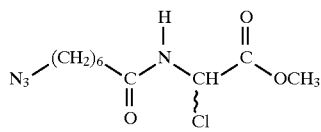
(XII)

($i_c$) reacting the resulting compound of formula XII with a chiral alcohol of determined (R) or (S) configuration, of the benzyl type of the formula

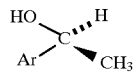
(XIII)

in which Ar is an aromatic radical, in a solvent of the halogenated hydrocarbon type, in the presence of a base, at a temperature between 10° and 40° C., for 5 to 50 hours, to give the compound of the formula

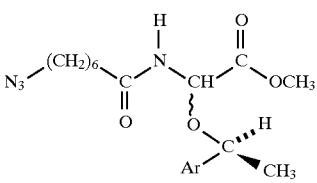
(XIV)

where Ar is as defined in the compound of formula XIII;

(ii) hydrolyzing the ester group of the resulting compound of formula XIV by reaction with a base in an aqueous medium, in a solvent of the ether type, at a temperature around room temperature, to give, after acidification, the acid compound of the formula

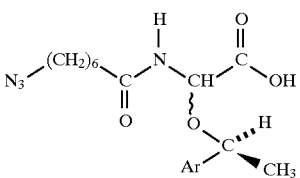
(XV)

in which Ar is as defined above;

(iii) reacting the resulting compound of formula XV with an amine of the formula

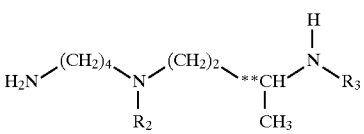
(VII)

in which $R_2$ and $R_3$ are an amino-protecting group sensitive to hydrogenation and **C is an asymmetric carbon of (R,S) or (R) configuration, in a solvent, in the presence of at least one coupling activator of a type known in peptide synthesis, at a temperature close to room temperature, for 10 to 75 hours, to give the compound of the formula

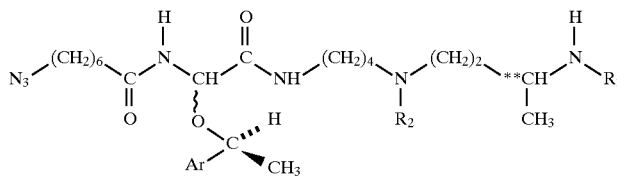
(XVI)

where Ar, $R_2$, $R_3$ and **C are as defined above;

(iv) separating the isomers of the compound of formula XVI, for example by means of chromatography on silica gel, to give each of the following two compounds separately:

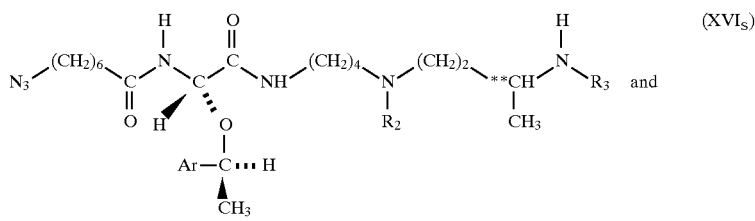

(XVI$_S$)

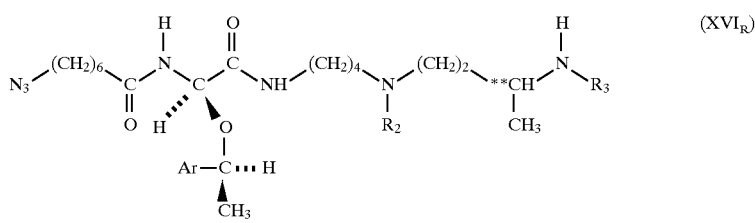

(XVI$_R$)

where Ar, R$_1$, R$_2$, R$_3$ and **C are as defined above; and (v) reacting the resulting compound of formula XVI$_S$ with triphenylphosphine, in the presence of water, in an anhydrous solvent, at a temperature between 50° and 70° C., for 10 to 30 hours, to give the corresponding intermediate amine, which is reacted in situ with the compound of the formula

(XVII)

in which R$_1$ is an amino-protecting group, to give, after reaction for 10 to 48 h at a temperature close to room temperature, the compound of formula II:

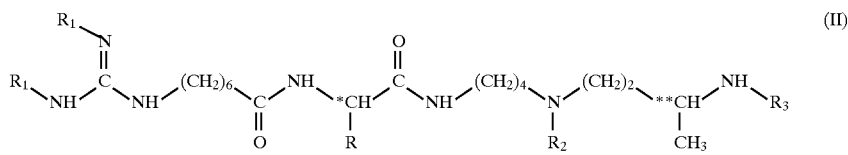

(II)

in which:

R is the group OR',

R$_1$, R$_2$ and R$_3$ are amino-protecting groups of the benzyloxycarbonyl type, R' is a group of the α-methylated benzyl type of the formula

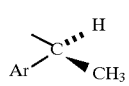

**C is an asymmetric carbon of (R,S) or (R) configuration, and

*C is an asymmetric carbon of (S) configuration; and (d) according to variant D:
  (i) taking a compound of formula XIV, obtained above according to the first step of the method of variant C, and separating its two diastereoisomers, especially by means of chromatography on silica gel, to give separately the two pure isomers of the formulae

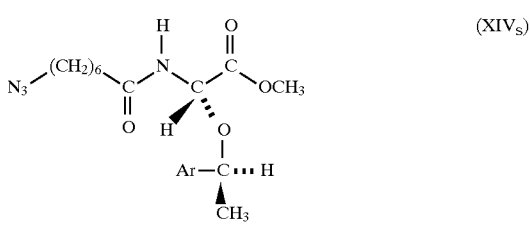

(XIV$_S$)

and

-continued

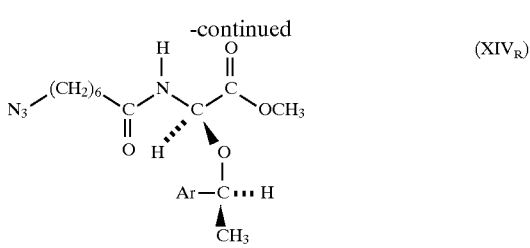

(XIV$_R$)

in which Ar is an aromatic radical as indicated above;

(ii) hydrolyzing the ester group of the resulting compound XIV$_S$, under conditions identical to those described in variant C, to give the corresponding acid of the formula

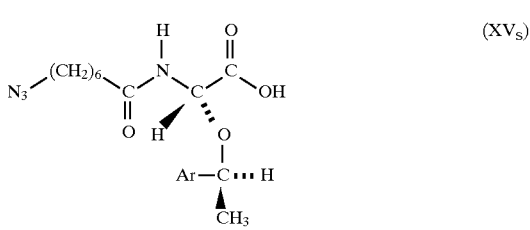

(XV$_S$)

in which Ar is as defined above;

(iii) reacting the resulting compound $XV_S$ with an amine of formula VII:

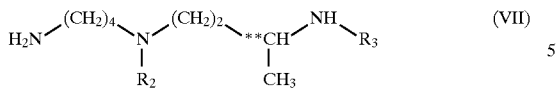

in which $R_2$ and $R_3$ are an amino-protecting group sensitive to hydrogenation and **C is a carbon atom of (R,S) or (R) configuration, under conditions identical to those described in variant C, to give the compound of the formula

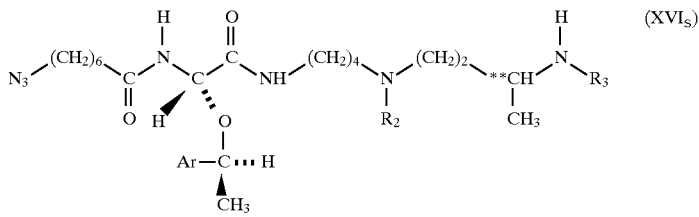

where Ar, $R_2$, $R_3$ and **C are as defined above; and then (iv) treating the resulting compound of formula $XVI_S$ in a manner analogous to step (v) of the method according to variant C to give the compound of formula II with the same characteristics as in the case of said variant C.

6. A method of preparing a compound of formula I in which the carbon atom *C is of (R) or (S) configuration, or one of its addition salts, comprising the step of:

obtaining, as an intermediate, a mixture of diastereoisomers of the formula

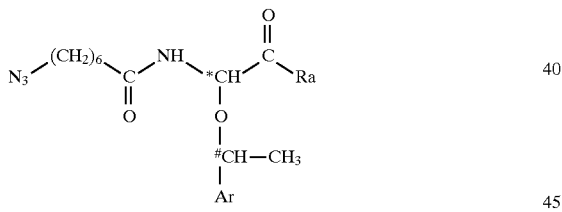

where:

Ar is an aromatic radical,

Ra is a $C_1$–$C_3$-alkoxy group or a group —HN—$(CH_2)_4$—N($R_2$)—$(CH_2)_2$—CH($CH_3$)—NH($R_3$) obtained by reaction with the amine of formula VII, $R_1$, $R_2$ and $R_3$, which are identical or different, are each an amino-protecting group,

*C is a carbon atom of (R,S) configuration, and

C is a carbon atom of (R) or (S) configuration; and separating the two isomers by methods known by those skilled in the art, for example preparative chromatography on silica gel, to give separately the compounds of the formulae

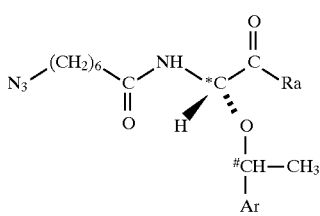

and

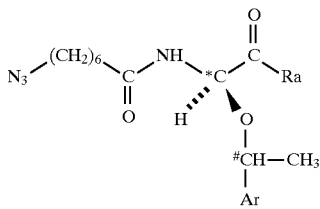

in which Ar, Ra and #C are as defined above.

7. A therapeutic composition comprising at least one compound selected from the group consisting of the compounds of formula I and non-toxic addition salts of the compounds of formula I, according to claim 1 and a physiologically acceptable excipient.

8. A method for treating immune disorders comprising administering to a patient in need thereof an immunosuppressive substance selected from the group consisting of the compounds of formula I and non-toxic addition salts of the compounds of formula I, according to claim 1.

9. A method of claim 8 wherein said immunosuppressive substance is administered with a physiologically acceptable excipient.

10. A method according to claim 5 wherein in variant A, step (ii), the ester group of the resulting compound of formula V is hydrolyzed by a known method wherein R is a group OR', where R' is $Si(CH_3)_2C(CH_3)_3$.

11. A method according to claim 5, wherein in variant C, step ($i_a$), said dehydrating agent is a molecular sieve.

12. A method for treating malaria comprising administering to a patient in need thereof an anti-malarial substance selected from the group consisting of the compounds of formula I and non-toxic addition salts of the compounds of formula I, according to claim 1.

13. A method of claim 12 wherein said anti-malarial substance is administered with a physiologically acceptable excipient.

14. A method for treating hyperreactive inflammatory diseases comprising administering to a patient in need thereof a substance active in treating hyperreactive inflammatory diseases selected from the group consisting of the compounds of formula I and non-toxic addition salts of the compounds of formula I, according to claim 1.

15. A method of claim 14 wherein the hyperreactive inflammatory disease is ulcerative colitis or asthma.

16. A method of claim 14 wherein said substance active in treating hyperreactive inflammatory diseases is administered with a physiologically acceptable excipient.

17. A method for analytical assay comprising using a compound of formula I and their acid addition salts according to claim 1 as a pharmacological reagent.

* * * * *